US008969543B2

(12) United States Patent
Jeong et al.

(10) Patent No.: US 8,969,543 B2
(45) Date of Patent: *Mar. 3, 2015

(54) SIRNA-HYDROPHILIC POLYMER CONJUGATES FOR INTRACELLULAR DELIVERY OF SIRNA AND METHOD THEREOF

(75) Inventors: Ji Hoon Jeong, Seoul (KR); Tae Gwan Park, Daejeon (KR); Sun-Hwa Kim, Daegu (KR)

(73) Assignees: Bioneer Corporation, Daejeon (KR); Samyang Biopharmaceuticals Corporation, Seoul (KR); Korea Advanced Institute of Science and Technology, Deajeon (KR)

( * ) Notice: Subject to any disclaimer, the term of this patent is extended or adjusted under 35 U.S.C. 154(b) by 222 days.

This patent is subject to a terminal disclaimer.

(21) Appl. No.: 11/651,011

(22) Filed: Jan. 9, 2007

(65) Prior Publication Data
US 2007/0287681 A1 Dec. 13, 2007

Related U.S. Application Data

(63) Continuation-in-part of application No. 10/551,466, filed as application No. PCT/KR03/00665 on Apr. 3, 2003.

(51) Int. Cl.
*C07H 21/04* (2006.01)
*C07H 21/02* (2006.01)
*A61K 48/00* (2006.01)

(52) U.S. Cl.
USPC ............................ 536/24.5; 536/23.1; 514/44

(58) Field of Classification Search
None
See application file for complete search history.

(56) References Cited

U.S. PATENT DOCUMENTS

| 4,904,582 | A | * | 2/1990 | Tullis ................................. 435/6 |
| 5,714,166 | A | | 2/1998 | Tomalia et al. |
| 6,221,959 | B1 | | 4/2001 | Kabanov et al. |
| 6,521,456 | B1 | | 2/2003 | Siebenkotten et al. |
| 2001/0005717 | A1 | | 6/2001 | Wagner et al. |
| 2004/0167090 | A1 | | 8/2004 | Monahan et al. |
| 2004/0249178 | A1 | * | 12/2004 | Vargeese et al. ............... 552/506 |
| 2004/0266707 | A1 | | 12/2004 | Leake et al. |
| 2006/0019298 | A1 | * | 1/2006 | Shima et al. ...................... 435/6 |
| 2007/0135370 | A1 | * | 6/2007 | MacLachlan et al. ........... 514/44 |
| 2010/0036115 | A1 | * | 2/2010 | Beigelman et al. .............. 540/95 |

FOREIGN PATENT DOCUMENTS

| CA | 2 619 533 A1 | 2/2007 |
| EP | 1 801 210 A2 | 6/2007 |
| WO | WO 02/43769 A2 | 6/2002 |
| WO | WO 2004/009769 A2 | 1/2004 |
| WO | WO 2004/044141 A2 | 5/2004 |
| WO | WO 2004/076630 A2 | 9/2004 |
| WO | WO 2004/087931 A1 | 10/2004 |
| WO | WO 2007/021142 A1 | 2/2007 |

OTHER PUBLICATIONS

Kim et al., Comparitive Evaluation of Target-Specific GFP Gene Silencing Efficiencies for Antisense ODN, Synthetic siRNA, and siRNA Plasmid Complexed with PEI-PEG-FOL Conjugate, 2006, Bioconjugate Chem, 17, pp. 241-244.*
Kim et al., PEG conjugated VEGF siRNA for anti-angiogenic gene therapey, 2006, Journal of Controlled Release, 116, pp. 123-129.*
Li et al., Folate-Mediated Targeting of Antisense Oligodeoxynucleotides to Ovarian Cancer Cells, 1998, Pharmaceutical Research, vol. 15, No. 10, pp. 1540-1545.*
Vinogradov et al., Polyion Complex Micelles with Protein-Modified Corona for Receptor-Mediated Delivery of Oligonucleotides into Cells, 1999, Bioconjugate Chem., 10, pp. 851-860.*
Bertrand et al., Comparison of antisense oligonucleotides and siRNAs in cell culture and in vivo, 2002, Biochemical and Biophysical Research Communications, 296, pp. 1000-1004.*
Paul et al., Effective suppression of small interfering RNA in human cells, 2002, Nature Biotechnology, vol. 29, pp. 505-508.*
Reich et al., Small interfering RNA (siRNA) targeting VEGF effectively inhibits ocular neovascularization in a mouse model, 2003, Molecular Vision, 9, pp. 210-216.*
Fisher et al., "Intracellular disposition and metabolism of fluorescently-labeled unmodified and modified oligonucleotides microinjected into mammalian cells," *Nucleic Acids Res.* 21:3857-3865, Oxford University Press (1993).
Kataoka et al., "Spontaneous formation of polyion complex micelles with narrow distribution from antisense oligonucleotide and cationic block copolymer in physiological saline," *Macromolecules* 29:8556-8557, American Chemical Society (1996).
Milligan et al., "Current concepts in antisense drug design," *J. Med. Chem.* 36:1923-1937, American Chemical Society (1993).
International Search Report for International Appl. No. PCT/KR2006/003229, mailed Jan. 4, 2007.
Written Opinion of the International Searching Authority for International Appl. No. PCT/KR2006/003229, mailed Jan. 4, 2007.
International Search Report for International Appl. No. PCT/KR03/000665, mailed Nov. 4, 2003.
International Preliminary Examination Report for International Appl. No. PCT/KR03/000665, completed Aug. 24, 2005.

(Continued)

*Primary Examiner* — Amy Bowman
(74) *Attorney, Agent, or Firm* — Sterne, Kessler, Goldstein & Fox P.L.L.C.

(57) ABSTRACT

The present invention is related to hybrid conjugates formed by covalently bonding siRNA (small interfering RNA) molecules to hydrophilic polymers for improving stability of the siRNA molecules effective for delivering the siRNA in vivo, and polyelectrolyte complex micelles formed by ionic interactions between the conjugates and multifunctional cationic compounds. The siRNA-hydrophilic polymer conjugates and polyelectrolyte complex micelles derived therefrom can be used for improving stability of the siRNA molecules in vivo. Consequently, the delivery of siRNA molecules for therapeutic applications into cells can be facilitated, and the siRNA is still active even though a small dose of the siRNA is used.

12 Claims, 16 Drawing Sheets

(56) References Cited

OTHER PUBLICATIONS

Bonora, "Polymer-conjugated Bioactive Oligonucleotides," *Journal of Bioactive and Compatible Polymers 17*:375-389 (Sep. 2002) Sage Publications.

Healy et al., "Pharmacokinetics and Biodistribution of Novel Aptamer Compositions," *Pharmaceutical Research 21*:2234-2246 (2004) Springer Science+Business Media, Inc.

Jeong et al., "Novel Intracellular Delivery System of Antisense Oligonucleotide by Self-Assembled Hybrid Micelles Composed of DNA/PEG Conjugate and Cationic Fusogenic Peptide," *Bioconjugate Chem. 14*:473-479 (Mar. 2003) American Chemical Society.

Jeong et al., "A New Antisense Oligonucleotide Delivery System Based on Self-Assembled ODN-PEG Hybrid Conjugate Micelles," *Journal of Controlled Release 93*:183-191 (Dec. 2003) Elsevier B.V.

Jones et al., "Conjugates of Double-Stranded Oligonucleotides with Poly(ethylene glycol) and Keyhole Limpet Hemocyanin: A Model for Treating Systemic Lupus Erythematosus," *Bioconjugate Chem. 5*:390-399 (1994) American Chemical Society.

Kawaguchi et al., "Stability, Specific Binding Activity, and Plasma Concentration in Mice of an Oligodeoxynucleotide Modified at 5'-Terminal with Poly(ethylene glycol)," *Biol. Pharm. Bull. 18*:474-476 (1995) Pharmaceutical Society of Japan.

Kim et al., "Target-Specific Gene Silencing by siRNA Plasmid DNA Complexed with Folate-Modified Poly(ethylenimine)," *Journal of Controlled Release 104*:223-232 (2005) Elsevier B.V.

Kim et al., "PEG conjugated VEGF siRNA for anti-angiogenic gene therapy," *Journal of Controlled Release 116*:123-129 (Available online Jun. 3, 2006) Elsevier B.V.

Lee et al., "Intracellular siRNA Delivery System Using Polyelectrolyte Complex Micelles Prepared from VEGF siRNA-PEG Conjugate and Cationic Fusogenic Peptide," *Biochemical and Biophysical Research Communications 357*:511-516 (Available online Apr. 9, 2007) Elsevier Inc.

Oishi et al., "Smart Polyion Complex Micelles for Targeted Intracellular Delivery of PEGylated Antisense Oligonucleotides Containing Acid-Labile Linkages," *ChemBioChem 6*:718-725 (2005) Wiley-VCH Verlag GmbH & Co. Weinheim.

Oishi et al., "Lactosylated Poly(ethylene glycol)-siRNA Conjugate through Acid-Labile β-Thiopropionate Linkage to Construct pH-Sensitive Polyion Complex Micelles Achieving Enhanced Gene Silencing in Hepatoma Cells," *J. Am. Chem. Soc. 127*:1624-1625 (2005) American Chemical Society.

Heyes, J., et al., "Cationic lipid saturation influences intracellular delivery of encapsulated nucleic acids," *Journal of Control Release 107*:276-287, Elsevier B.V., Netherlands (2005).

*Trans*IT-TKO® siRNA Transfection Reagent, Lit. # FAQ003 Rev. Jan. 4, 2006[online], Mirus, Apr. 1, 2006 [retrieved on Jun. 20, 2011]. Retrieved from Internet: <URL: http://www.mirusbio.com/assets/cms_files/faqs/FAQ003.pdf.>.

Muratovska, A. and Eccles, M.R., "Conjugate for efficient delivery of short interfering RNA (siRNA) into mammalian cells," *FEBS Letters 558*:63-68, Elsevier B.V., Netherlands (2004).

Pouton, C.W., et al., "Polycation-DNA complexes for gene delivery: a comparison of the biopharmaceutical properties of cationic polypeptides and cationic lipids," *Journal of Controlled Release 53*:289-299, Elsevier Science B.V., Netherlands (1998).

* cited by examiner

SIRNA-HYDROPHILIC POLYMER CONJUGATES FOR INTRACELLULAR DELIVERY OF SIRNA AND METHOD THEREOF

CROSS-REFERENCE TO RELATED APPLICATIONS

This application is a continuation-in-part of U.S. application Ser. No. 10/551,466 which is a national phase entry of International Appl. No. PCT/KR2003/000665, filed Apr. 3, 2003, both of which are incorporated herein in their entirety by reference.

BACKGROUND OF THE INVENTION

1. Field of the Invention

The present invention relates to conjugates between siRNA (small interfering RNA) molecules and hydrophilic polymers, which can effectively be used for delivering an siRNA for treatment of cancers and other infectious diseases, and polyelectrolyte complex micelles formed by ionic interactions between the conjugates and multifunctional cationic compounds.

2. Description of the Related Art

Safe and effective gene transfer techniques for gene therapy have been studied for a long time, resulting in development of various gene transfer vehicles and gene delivery systems. In particular, vectors based on adenoviruses and retroviruses, and nonviral vectors using liposomes, cationic lipids and cationic polymers have been developed as gene transfer vehicles. However, there are significant problems when viruses are used as vehicles for transfer of therapeutic genes into target cells. There is no evidence that the transferred genes cannot lead to the malfunction of host genes and/or the activation of oncogenes after integration into the host chromosome. In addition, if viral genes are continuously expressed even at a small amount, autoimmune response can be induced. Moreover, if a variant of the virus used as a gene transfer vehicle emerges in a host, the host can become infected with the variant virus, and the host immune system cannot effectively protect itself from the variant virus. For these reasons, rather than the viral vectors, gene delivery systems using liposomes, cationic lipids, or polymers are preferred, and related studies are aiming to improve drawbacks of each system. Such nonviral gene transfer vectors are less effective than the viral vectors, but are advantageous in terms of safety due to their mild side effects and being economical due to low cost production, thereby allowing industrial production of improved nonviral vectors.

The most important emerging approach in drug delivery system and gene delivery system now is a target specific delivery. When a drug is administered directly in vivo, every organ and every cell of a human body are equally attacked by the drug, and this, desired or not, damages normal cells and tissues as well as damaged or infected ones. To prevent such a problem, a large amount of research into drug delivery systems (DDS) has been performed to develop a technique used for selective delivery of drugs and genes. For example, a typical tissue/cell specific ligand such as folate, galactose, antibody and the like can be introduced directly into a drug or be conjugated with a drug transporter, so that delivery efficiency can be maximized while side effects of the drug on normal cells can be minimized. The delivery efficiency in a cell is expected to be maximized by employing such tissue/cell specific ligands to the preparation of a transporter for developing a gene-based therapeutic agent.

Meanwhile, a micelle is spontaneously formed by self-assembly of molecules having both hydrophilic and hydrophobic moieties at a specific ratio in an aqueous environment to maximize thermodynamic stability. The inside of the micelles is hydrophobic and thus can easily entrap water-insoluble drugs, and the surface of the micelles is hydrophilic and thus the micelle system facilitates solubilization of the water-insoluble drugs, drug delivery carrier and so on. Micelles having the hydrophobic core and the hydrophilic shell are stabilized in an aqueous environment by hydrophobic interaction, or stabilization of micelles can be achieved by ionic interaction between polyelectrolytes having opposite charges. A polyethylene glycol (PEG)-conjugated polyelectrolyte spontaneously associates with another polyelectrolyte having an opposite charge to form complex having a micellar structure, which are called polyelectrolyte complex micelles (Kataoka, K., et al., *Macromolecules* 29:8556-8557 (1996)). The polyelectrolyte complex micelles are more attractive than other drug delivery systems, such as microspheres or nanoparticles, due to there properties of having a very small size and a very uniform size distribution, and being a self-associated structure, thereby facilitating quality control and reproduction of pharmaceutical preparations.

Polymers used for drug delivery to a body should be biocompatible. A representative example of such biocompatible polymers is PEG. PEG, which has been approved for in vivo use by the U.S. Food and Drug Administration (FDA), has been utilized for a long time in a broad range of applications from improvement of protein characteristics, surface modification of polymers, and gene delivery. PEG, which is one of the most widely used biocompatible polymers, has excellent water solubility, and low toxicity and immunogenicity. In addition, PEG can strongly inhibit absorption of proteins to the polymers used in drug delivery by modifying the surface properties of the polymers.

Meanwhile, siRNA is a substance having generated a lot of interest as a gene-based therapeutic agent ever since it has been reported to have an excellent inhibitory effect of the expression of a specific gene in a zooblast (animal cell). In effect, because of its high activity and precise gene selectivity, siRNA is expected to be an alternative therapeutic agent to an antisense oligonuceotide (ODN) currently being used as a therapeutic agent as a result of 20-years of research. The siRNA is a short, double-helix RNA strand which can suppress expression of a targeted mRNA having complementary base sequence to the siRNA.

siRNA has very low stability and is quickly degraded in vivo, thus its therapeutic efficiency deteriorates quickly. Even though the dose of expensive siRNA can be increased, the anionic nature of siRNA hinders it from permeating a cell membrane with negative charge, leading to low levels of siRNA transfer into intracellular compartments (Celia M. et al., *Chemical and Engineering News* December 22:32-36 (2003)). In addition, although siRNA is double stranded, the linkage of a ribose sugar in the RNA is chemically very unstable compared with that of a deoxyribose sugar in the DNA. Thus, the majority of siRNA has a half-life of about 30 minutes in vivo and is quickly degraded.

According to a recent study into the enhancement of stability of siRNA, various functional groups have been introduced into siRNA to protect the siRNA from lyases (Frank Czauderna et al., *Nucleic Acids Research* 31:2705-2716 (2003)). Nevertheless, the technology for securing the stability and effective cell membrane permeability of siRNA is still in development phases. The study also suggested that because of the instability of siRNA molecules in blood high-concentrations of siRNA should be continuously introduced in order to get therapeutic effects of the siRNA. Unfortunately however, this method is reported to be highly inefficient. Even from an economic aspect, there is a need to develop technology for a novel transporting agent that facilitates intracellular transfer of siRNA as a gene-based therapeutic agent.

SUMMARY OF THE INVENTION

It is an object of the present invention to provide a conjugate of an siRNA molecule and a biocompatible hydrophilic polymer to enhance the efficiency of intracellular delivery of siRNA, wherein the polymer is conjugated at the end of a sense strand or an antisense strand of the siRNA through a degradable or non-degradable linkage.

It is another object of the present invention to provide a polyelectrolyte complex micelle produced by interaction between the conjugates of the present invention and cationic compounds.

To achieve the above objects and advantages, there is provided an siRNA-hydrophilic polymer conjugate covalently linked to each other, represented by the following formula:

P—X—Y wherein P is a hydrophilic polymer, X is a linker-nonmediated covalent bond or linker-mediated covalent bond, and Y is an siRNA molecule.

In some embodiments of the present invention, the siRNA has a molecular weight ranging from 10,000 to 30,000. Within this range, siRNA comprises 19 to 30 nucleotides, or in some embodiments 19 to 23 nucleotides. In some embodiments, the non-limiting examples of the siRNA decreases or down-regulate expression of, or can be originated from, c-myc, c-myb, c-fos, c-jun, c-raf, c-src, bcl-2, vascular endothelial growth factor (VEGF), VEGF-B, VEGF-C, VEGF-D, or PIGF.

In addition, in some embodiments the hydrophilic polymer can be originated from a nonionic polymer having a molecular weight ranging from 1,000 to 10,000. The non-limiting examples of the hydrophilic polymer can include a nonionic hydrophilic polymer such as PEG, polyvinylpyrolidone, polyoxazolin, or combinations thereof.

In addition, the covalent linkage (i.e., X in the formula) can be either a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

In some embodiments, the siRNA-hydrophilic polymer conjugate of the present invention can further introduce a cell-specific ligand at the end of the conjugate. The cell-specific ligand can include, but is not limited to, a cell-specific antibody, cell-specific peptide, cell growth factor, folate, galactose, mannose, RGD, or transferrin.

In other aspects, the present invention provides a method of preparing an siRNA-hydrophilic polymer conjugate in the form of P—X—Y by covalently bonding a hydrophilic polymer to the end group of an siRNA molecule, the method comprising: selecting a predetermined siRNA molecule; and covalently bonding the siRNA molecule to a hydrophilic polymer, wherein P is a hydrophilic polymer, X is a linker-nonmediated covalent bond or linker-mediated covalent bond, and Y is an siRNA molecule.

In some embodiments, the method of preparing an siRNA-hydrophilic polymer conjugate can further comprise activating a functional group of siRNA, and the covalently bonding can comprise activating the functional group of siRNA, and covalently bonding the activated functional group to a hydrophilic polymer. The functional group to be activated can include, but is not limited to, an amine group, thiol group, phosphate group, or combinations thereof. In some embodiments, the material which activates the functional group of siRNA comprises 1-ethyl-3,3-diethylaminopropyl carbodiimide, imidazole, N-hydroxylsuccinimide, dichlorohexylcarbodiimide, N-β-maleimidopropionic acid, N-β-maleimidopropyloxylsuccinimide ester, N-succinimidylpyridyldithiopropionate, or combinations thereof.

FIG. 1 schematically shows the procedure of forming a conjugate between an siRNA molecule and a hydrophilic polymer, such as PEG. As shown, a primary amine group at the 3'-end of a sense strand of a double-stranded siRNA reacts with a heterofunctional bonding agent, such as an active NHS group of N-succinimidyl-3-(2-pyridyldithio)-propionate (hereinafter, abbreviated simply as SPDP) to produce an activated siRNA with 2-pyridyldisulfide. Then methoxy-PEG (mPEG-SH) with the sulfhydryl group at the terminal is added to the siRNA activated with 2-pyridyl disulfide. By the sulfhydryl-disulfide exchange reaction, an siRNA-S—S-PEG conjugate (siRNA-PEG) linked with a disulfide bond (—S—S—) is formed.

Still other aspects of the present invention provide polyelectrolyte complex micelle formed by ionic interaction between siRNA-hydrophilic polymer conjugates and cationic compounds. The cationic compound can include, but is not limited to, a cationic peptide, cationic lipid, cationic polymer, or combinations thereof.

The non-limiting examples of the cationic peptide can include KALA (lysine-alanine-leucine-alanine), polylysine, protamine, or combinations thereof, those of the cationic lipid can include dioleyl phosphatidylethanolamine, cholesterol dioleyl phosphatidylcholine, or combinations thereof, and those of the cationic polymer can include polyethylene imine (hereinafter, abbreviated simply as PEI), polyamine, polyvinylamine, or combinations thereof.

In addition, the present invention provides a method of preparing polyelectrolyte complex micelle, comprising: preparing the siRNA-hydrophilic polymer conjugates; and mixing the conjugates with cationic compounds.

In detail, conjugates obtained by covalently bonding an siRNA to a biocompatible hydrophilic polymer are mixed with polyvalent cationic polymers, lipids or peptides, producing the polyelectrolyte complex micelle of the present invention by ionic interaction. The siRNA-hydrophilic polymer conjugate and the polyelectrolyte complex micelle thus obtained serves to improve intracellular delivery of siRNA, and can be utilized for the treatment of various diseases. More details on the synthesis of conjugates, formation of polyelectrolyte complex micelles, properties thereof, intracellular delivery efficiency and therapeutic effects on disease models will be provided later on.

Still another aspect of the present invention provides a method for delivering an siRNA to an animal in need thereof comprising: preparing a polyelectrolyte complex micelle comprising the siRNA-hydrophilic polymer conjugate; and introducing the polyelectrolyte complex micelle into an animal. Although there is no limit to the kind of animal, in some embodiments the method for delivering an siRNA of the present invention is for delivering to a human. However, it is evident that the method is equally applicable to animals other than humans.

Yet another aspect of the present invention provides a pharmaceutical composition comprising the siRNA-hydrophilic polymer conjugates or the polyelectrolyte complex micelle and a pharmaceutically acceptable carrier.

For better administration, the composition can further contain at least one kind of pharmaceutically acceptable carrier in addition to the above-described active ingredients. It is important that the pharmaceutically acceptable carriers be compatible with the active ingredients of the present invention. Examples of such carriers include saline solution, sterile water, Ringer's solution, buffered saline solution, dextrose solution, maltodextrin (aqueous) solution, glycerol, ethanol and mixtures thereof. If needed, typical additives, such as, an antioxidant, a buffer, a bacteriostatic agent and the like, can be added. Moreover, the composition can be pharmaceutically produced for injection in the form of an aqueous solution, suspension, emulsion and so forth by adding more additives, such as, a diluting agent, a dispersing agent, a surfactant, a bonding agent and a lubricant. Further, the composition can be prepared for pharmaceutical application depending on the types of disease or the ingredient, by employing conventional methods or the methods described in *Remington's Pharmaceutical Science* (18th Ed., 1995), Mack Publishing Company, Easton Pa.

The pharmaceutical composition of the present invention can be defined by an expert in the technical field in which the invention applies, based on a typical symptom of a patient and the seriousness of the disease. The composition can be prepared in diverse forms, such as, powder, tablet, capsule, solution, injection, ointment, syrup and the like, and provided to patients in single dose container or multi-dose container, for example, in a sealed ampoule or bottle.

The pharmaceutical composition of the invention can be administered orally or parenterally. Even though there is no limit to the administration route of the pharmaceutical composition, the composition can be brought into contact with the body through diverse administration routes, including oral administration, intravenous administration, intramuscular administration, intra-arterial administration, intramedullary administration, intrathecal administration, intracardiac administration, percutaneous administration, hypodermic administration, intraperitoneal administration, enteral administration, sublingual administration, and topical administration.

For such clinical administration, the pharmaceutical composition of the present invention can be prepared in an adequate product using conventional techniques. For instance, if the composition needs to be administered orally, it can be mixed with an inactive diluting agent or an edible carrier, be sealed in hard or soft gelatin capsules, or be pressed into tablets. In case of oral administration, active compounds are mixed with an excipient and are used in form of tablets for intake, buccal tablets, troches, capsules, elixir, suspension, syrup, wafers and the like. On the other hand, in case that the pharmaceutical composition of the present invention is injected or administered parenterally, it can be produced using well-known methods of the technical field in which the invention applies or any conventional methods. Dosage of the composition varies depending on a patient's body weight, age, sex, health conditions, diet, timing of administration, administration method, evacuation rate, the seriousness of a disease, etc, and can be determined by one of ordinary skill in the art, e.g., a physician, physician assistant, nurse practitioner, or pharmacist.

DETAILED DESCRIPTION OF THE INVENTION

Figure 1:
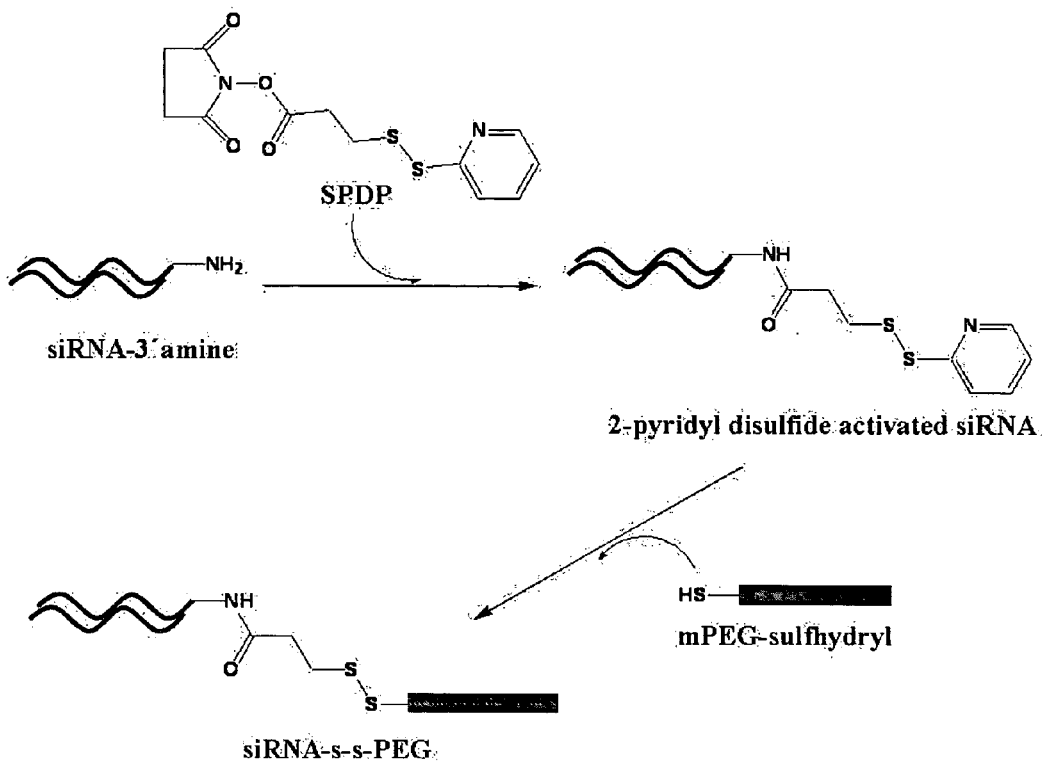
FIG. 1 is a schematic view briefly describing a conjugation procedure between an siRNA molecule and a hydrophilic polymer, PEG containing a cleavable disulfide bond in a cell.

The present invention can be understood more readily by reference to the following detailed description of the invention and the Examples included herein.

In some embodiments, the present invention is directed to an siRNA-hydrophilic polymer conjugate wherein siRNA and hydrophilic polymer are covalently linked each other, and have the structure represented by the following formula:

wherein P is a hydrophilic polymer, X is a linker-nonmediated covalent bond or linker-mediated covalent bond, and Y is an siRNA molecule.

In a conjugate of the present invention, the hydrophilic polymer (P) can be originated from a nonionic polymer having molecular weight ranging from 1,000 to 10,000. The non-limiting examples of the hydrophilic polymer can include a nonionic hydrophilic polymer such as PEG, polyvinylpyrolidone, polyoxazolin, or combinations thereof. Within the range of molecular weight, in some embodiments it is suitable to enhance the stability of the conjugate formed by the cationic polymer and siRNA in blood.

The functional group of a hydrophilic polymer can be substituted by other functional groups. For example, hydroxyl group (—OH) can be substituted with sulfhydryl group (—SH), carboxyl group (—COOH), or amine group (—NH$_2$). Among the hydrophilic polymers, PEG can be used for the synthesis of conjugate of the present invention in that PEG has an end to which diverse molecular weights and functional groups can be introduced, is highly anthrophophilic, does not induce an immunological reaction, and increases solubility in water, thereby improving gene delivery efficiency in vivo. At the time of conjugation between the siRNA and a hydrophilic polymer, PEG is desirably conjugated to the siRNA at the 3' end of the sense strand in order to minimize the decrease of RNAi effect by the siRNA.

In some embodiments of the present invention, the siRNA has a molecular weight ranging from 10,000 to 30,000. Within this range, siRNA can be a double-stranded oligomer form comprising 19 to 30 nucleotides, or in some embodiments, 19 to 23 nucleotides, and can have an inhibitory activity for the expression of target gene. The siRNA of the present invention can be any of those which could be used for therapeutic or research purposes. The non-limiting examples of the siRNA can be an siRNA that decreases or down-regulates expression of, or is originated from, any gene having possibility of using in delivering an siRNA, e.g., gene therapy, for example, c-myc, c-myb, c-fos, c-jun, c-raf, c-src, bcl-2 or VEGF, VEGF-B, VEGF-C, VEGF-D, or PlGF.

In one example of the present invention, hVEGF siRNA was used to suppress a VEGF expression. VEGF binds to a VEGF receptor existing on the surface of a human vascular endothelial cell, and serves to promote the growth and migration of the endothelial cells, thereby promoting the neovascularization. Especially, since cancer cell growth or metastasis is closely related to the neovascularization, suppression of the neovascularization for the purpose of inhibiting cancer cell growth has drawn a lot of attention as a new method for the treatment of cancer.

The 3' end group of the sense or antisense strand of the siRNA can be substituted by another functional group. For example, the hydroxyl group at the 3' end of the siRNA can be substituted by an amine group, sulfhydryl group, or phosphate group.

The conjugate of the present invention has a P—X—Y structure, in which X denotes a linker or simply a covalent bond that covalently bonds a hydrophilic polymer (P) to a residue derived from the siRNA (Y). There is no limit to the linker mediating the covalent bond between the hydrophilic polymer and the end group of the residue derived from the siRNA as long as it is degradable on necessity under predetermined conditions. Namely, any compound that activates the siRNA and/or the hydrophilic polymer during the synthesis of their conjugates can be used to make the linker X. For example, suppose that SPDP, an activation substance, is bonded to the siRNA having an amine at the 3' end to produce an activated siRNA, so that the amine at the end can be activated to a pyridyldithiol group. By using this activated siRNA as a raw material (or reactant) and using modified PEG (SH-PEG) having a sulfhydryl group as the hydrophilic polymer unit (P), the structure of X in the conjugate becomes —NH—CO—CH$_2$—CH$_2$—S—S—. In other words, the X can be a residual portion (linker) resulting from the activation process of the reactants, i.e., the hydrophilic polymer and the siRNA during preparing the conjugates, or simply a covalent bond without a linker between the hydrophilic polymer and the functional group of the siRNA in case the reaction does not require activation. The X can be varied depending on targets to which siRNA is delivered, and is either a non-cleavable linkage or a cleavable linkage. The non-cleavable linkage can include, but is not limited to, an amide bond or phosphate bond, and the cleavable linkage can include disulfide bond, acid-cleavable linkage, ester bond, anhydride-cleavable bond, biodegradable bond, or enzyme-cleavable linkage. In some embodiments, X is a disulfide bond.

In the case that the siRNA comprises long nucleotide chains (or strands) with molecular weight of about 30,000 for example, two strands of siRNA oligomers can stably be incorporated into the RNA-induced silencing complex (RISC), an enzyme complex in a cell involved in inhibition of gene expression, in spite of the presence of a hydrophilic polymer conjugated to siRNA. Meanwhile, in the case that the siRNA has 19 nucleotides with molecular weight of about 10,000, its structural stability, during its incorporation into the RISC in the cell, can be decreased by a hydrophilic polymer introduced to the end of siRNA. Thus, it is desirable to introduce cleavable linkage capable of decomposing in vivo or in a cell. Examples of such a bond can include a disulfide bond that is cleaved in a cell by glutathione existing in a great amount in cytoplasm, an acid-cleavable linkage that is easily and effectively cleaved in an acidic environment after entering a cell, an ester bond that is easily and effectively cleaved after entering a cell, an anhydride bond, and an enzyme-cleavable linkage that is cleaved by enzymes existing around a specific cell right before entering the cell.

Figure 10:
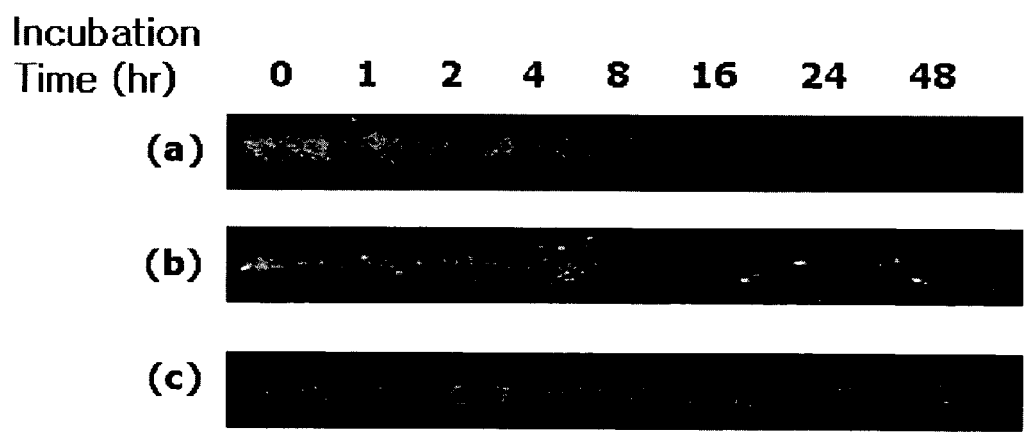
FIG. 10 is a photograph showing the stability of (a) naked siRNA, (b) siRNA-PEG conjugate, and (c) siRNA-PEG/PEI polyelectrolyte complex micelles. The samples were incubated in the medium containing 50% FBS at 37° C.

It was reported that the chemical modification of siRNA reduced the corresponding RNAi activity from 10% to 50% depending on where it was structurally altered and also elicited cellular toxicity to some extent (Amarzguioui, M. et al., *Nucleic Acids Res.*, 31:589-595 (2003)). In some embodiments of the present invention, to minimize the loss of RNAi activity from the conjugation of hydrophilic polymer such as PEG, hydrophilic polymer was conjugated to the 3' end of a sense strand of siRNA and a cleavable disulfide bond was introduced between siRNA and hydrophilic polymer to allow the release of an intact siRNA under a reductive intracellular environment (see FIG. 4). In the cytosolic environment, more than 98% of intracellular glutathione is maintained in a reduced thiol form (GSH) due to the presence of glutathione disulfide (GSSG) reductase (Wang, W. et al., *Pharmacol. Rev.*, 50:335-356 (1998)). The disulfide linkage between siRNA and hydrophilic polymer could readily be cleaved by intracellular GSH, which generated an intact siRNA (see FIG. 10). In the cytosol, the cleaved siRNA molecules are first encountered to interact with RISC proteins to initiate a series of RNAi processes. In this sense, the intracellular regeneration of an intact siRNA would fully maintain RNAi activity and specificity. In case of conjugating siRNA with hydrophilic polymer such as PEG, the disulfide bond can be used in view of the structure of conjugate. PEG introduced to the 5'-end of sense strand of siRNA could be separated from siRNA in the cell, which does not prevent the complex formation between siRNA and RISC.

Figure 22:
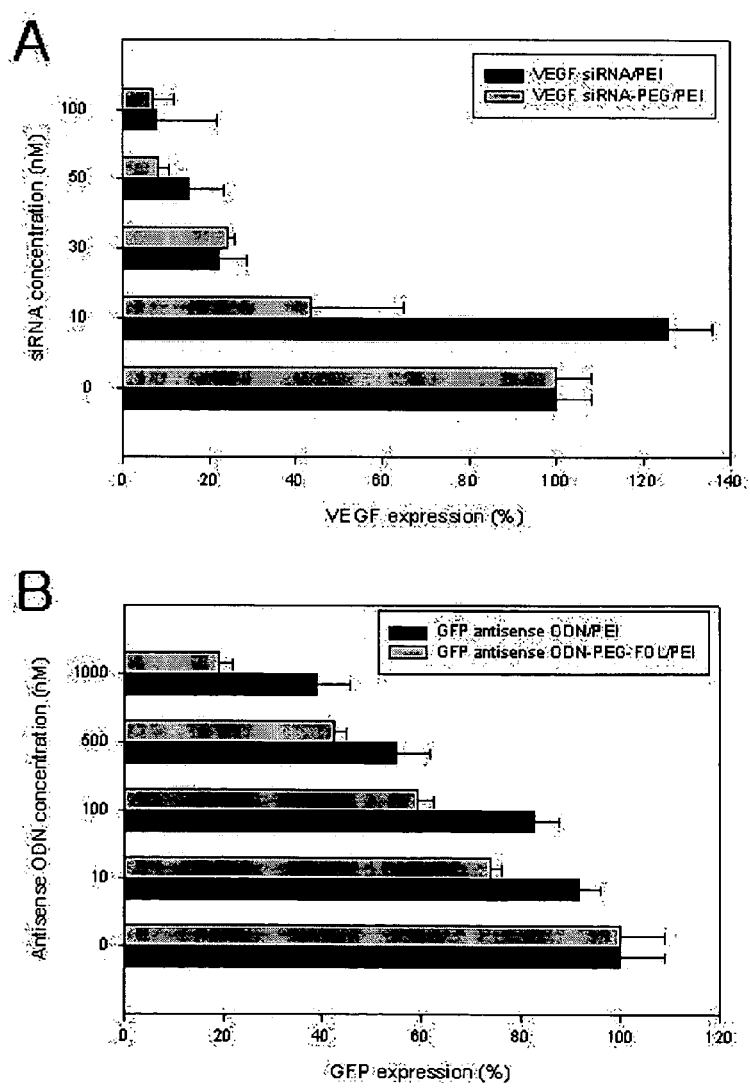
FIG. 22 is a graph comparing gene inhibitory effects between an siRNA polyelectrolyte complex, (A), and an oligodeoxynucleotide (ODN) polyelectrolyte complex, (B).

Antisense ODN/PEG/PEI polyelectrolyte complex micelles can be prepared by conjugating antisense oligodeoxynucleotide (ODN) and PEG with a non-cleavable linkage (Jeong, J. H. et al., *Bioconjug. Chem.*, 16:1034-1037 (2005)). The antisense ODN has very different gene suppression mechanism from that of siRNA. Unlike the siRNA, ODN does not bind to protein complexes, but binds directly to a target mRNA sequence and degrades it. Thus, it is not absolutely necessary for the ODN to be separated from a hydrophilic polymer (Kalota, A. et al., *Cancer Biol. Ther.* 3:4-12, (2004)). On the other hand, in case that the siRNA is conjugated to a hydrophilic polymer, the hydrophilic polymer can provide considerable steric hindrance against the formation of siRNA-RISC complexes. Therefore, to show siRNA activity fully, it is desirable to separate the siRNA from the hydrophilic polymer. That is, in case that the PEG and the antisense ODN are bonded covalently, introduction of a cleavable linkage is not absolutely required. Meanwhile, in case of the siRNA, introduction of a cleavable linkage is important for the introduction of PEG. Moreover, since the siRNA has a relatively higher specificity to target gene than the antisense ODN, the side effects of nonselective inhibition of other genes are considerably reduced and a specific target gene can be inhibited very effectively using the siRNA with only 1/10 dose of the antisense ODN (see FIG. 22). When the dose is reduced, the burden on a body at the time of clinical administration of the siRNA polyelectrolyte complex micelles in forms of pharmaceutical composition can be reduced, and the overall cost is cut down. In addition, unlike the ODN-derived polyelectrolyte complex using single-stranded DNA molecules, the siRNA-derived polyelectrolyte complex uses double-stranded RNA molecules, so its stability is much better than the ODN-PEG polyelectrolyte complex. In short, the siRNA polyelectrolyte complex of the present invention shows outstanding advantages on selectivity, dose, and stability of target mRNA, compared with the conventional DNA-based ODN polyelectrolyte complex.

The siRNA-hydrophilic polymer conjugate of the present invention can introduce cell-specific ligand at the end of the conjugate. In some embodiments, the cell-specific ligand can be selected from cell-specific antibody, cell-specific peptide, cell growth factor, folate, galactose, mannose, RGD or transferrine, and the line. This ligand can be introduced to the end of the conjugate, in some embodiments to the OH group at the end of PEG through disulfide bond, amide bond, or ester bond.

Moreover, the present invention provides a method of preparing an siRNA-hydrophilic polymer conjugate in the form of P—X—Y by covalently bonding a hydrophilic polymer to the end group of the siRNA. Here, P is a hydrophilic polymer, X is a covalent bond or linker-mediated covalent bond, and Y is an siRNA molecule.

The method of preparing an siRNA-hydrophilic polymer conjugate can further comprise activating a functional group of siRNA or hydrophilic polymer. The functional group to be activated can be an amine group, thiol group, phosphate group, or combinations thereof. The material which activates the functional group of siRNA can be 1-ethyl-3,3-diethylaminopropyl carbodiimide, imidazole, N-hydrosuccinimide and dichlorohexylcarbodiimide, N-β-maleimidopropionic acid, N-β-maleimidopropyloxylsuccinimide ester, N-succinimidylpyridyldithiopropionate, and combinations thereof.

There is no specific limit to the reaction conditions between a hydrophilic polymer and an siRNA molecule, but the reaction is typically carried out at room temperature for about 24 hours to about 48 hours. Although the mixing ratio of the reactant required for the reaction is not specified, the mole ratio (%) of the hydrophilic polymer to the siRNA molecule lies in the range of 10:90 to 90:10, through which the ratio of the hydrophilic polymer introduced into the siRNA molecule can be adjusted.

Figure 2:
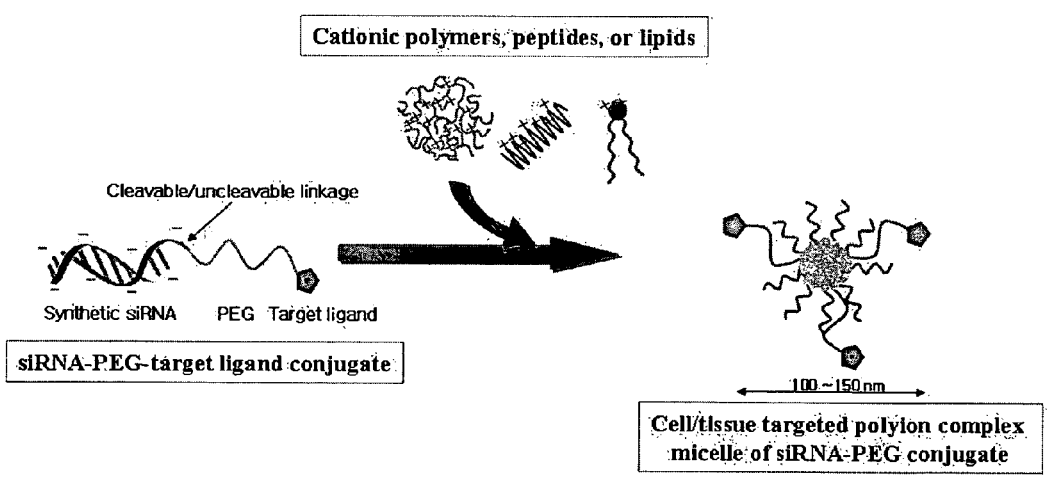
FIG. 2 is a schematic view briefly describing the concept of the siRNA polyelectrolyte complex micelles.

The hydrophilic polymer-siRNA conjugate of the present invention can be used as a component of the polyelectrolyte complex micelle. The polyelectrolyte complex micelle is a self-assembling, aggregate molecule from an interaction between an siRNA conjugated to a nonionic hydrophilic polymer and its oppositely charged polymer (for example, cationic compound), and can have a size of about 100 nm to about 200 nm (see FIG. 2). A nucleus produced by an ionic interaction between an siRNA molecule and a cationic compound exists at the core of the micelle, and an outer surface layer of the micelle is composed of a hydrophilic polymer moiety.

In the present invention, the non-limiting examples of the cationic compound can be a cationic peptide such as KALA, polylysine, or protamine, a cationic polymer such as PEI, polyamine, polyvinylamine, or a cationic lipid such as dioleyl phosphatidylethanolamine, or cholesterol dioleyl phosphatidylcholine.

The following will now explain a method of preparing such a micelle. First, an siRNA-hydrophilic polymer conjugate is diluted in a phosphate buffer, and is mixed with a cationic compound to form polyelectrolyte complex micelle in an aqueous solution. To stabilize micelle, the mixture is laid aside at room temperature for several tens of minutes. Desirably, the amount of the cationic compound being added is adjusted so as to make the ratio of positive charges in the cationic compound to negative charges of the siRNA falls in the range of 1: (N/P=1/1) to 24:1 (N/P=24/1).

Figure 6:
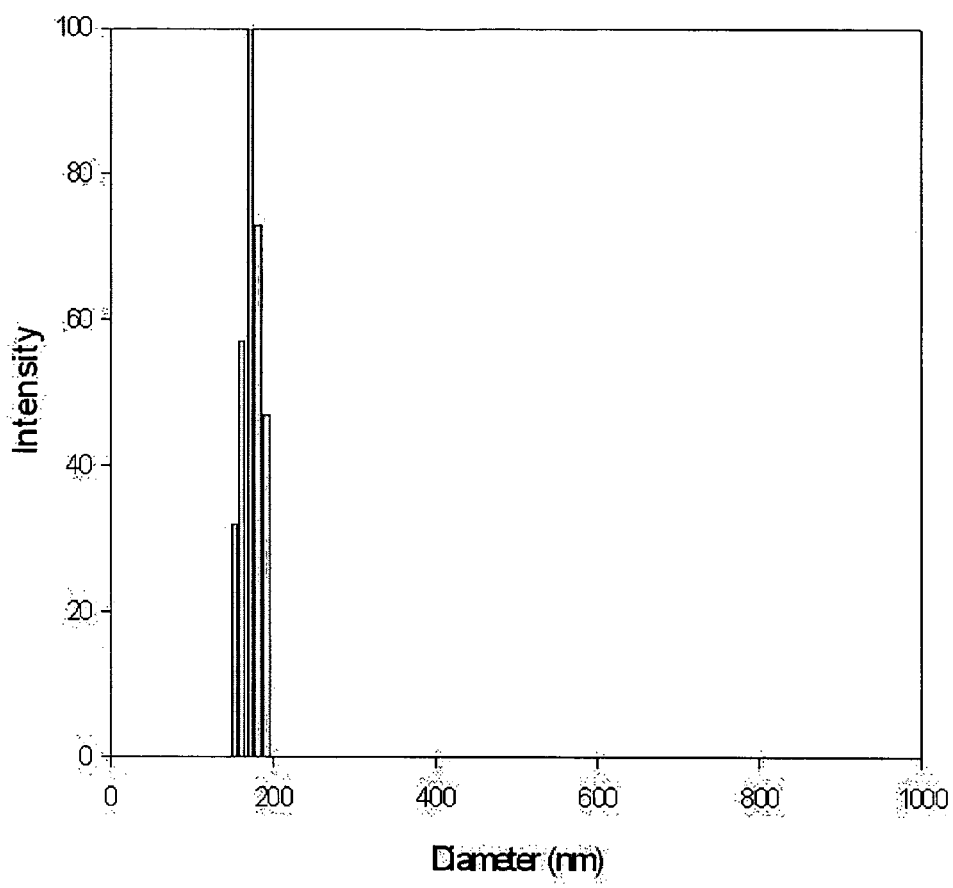
FIG. 6 is a graph showing a size of siRNA-PEG/KALA (cationic peptide) polyelectrolyte complex micelle, measured by DLS method.

According to one embodiment of the present invention, to form polyelectrolyte complex micelle facilitating the intracellular delivery of the siRNA-PEG conjugate in vivo, a cationic peptide KALA was used. When the size of an siRNA-PEG/KALA polyelectrolyte complex micelle in the aqueous solution was measured by a dynamic light scattering (DLS) method, the micelles were found to have a very narrow size distribution with a size of about 150 nm (FIG. 6).

In addition, to evaluate siRNA stability of the siRNA-PEG/KALA polyelectrolyte complex micelle in vivo, the siRNA stability of an siRNA-PEG conjugate was compared with a naked siRNA. It turned out that the stability was good for 24 hours in case the PEG had been introduced into the siRNA, and was drastically improved when polyelectrolyte complex micelles were formed (see FIG. 7).

In another embodiment of the present invention, the effect of VEGF siRNA-PEG/KALA polyelectrolyte complex micelles on the expression of vascular endothelial growth factor (VEGF) was examined using a human prostate cancer cell line (PC-3). It was observed that when the PC-3 cell line was treated with VEGF siRNA/KALA and VEGF siRNA-PEG/KALA polyelectrolyte complex micelles, the expression of VEGF was significantly suppressed (see FIG. 8).

In addition, to find out the extent of the inhibitory activity of VEGF siRNA-PEG/KALA polyelectrolyte complex micelles on the proliferation of cancer cells in vivo, the human cancer cells were grafted into a mouse and an siRNA formulation was administered to the mouse through its blood vessel. When the degree of proliferation of the cancer cell line was observed, the siRNA-PEG/KELA polyelectrolyte complex micelles exhibited considerable suppression effects on the growth of the cancer cell line grafted into the animal model (see FIG. 9).

Figure 11:
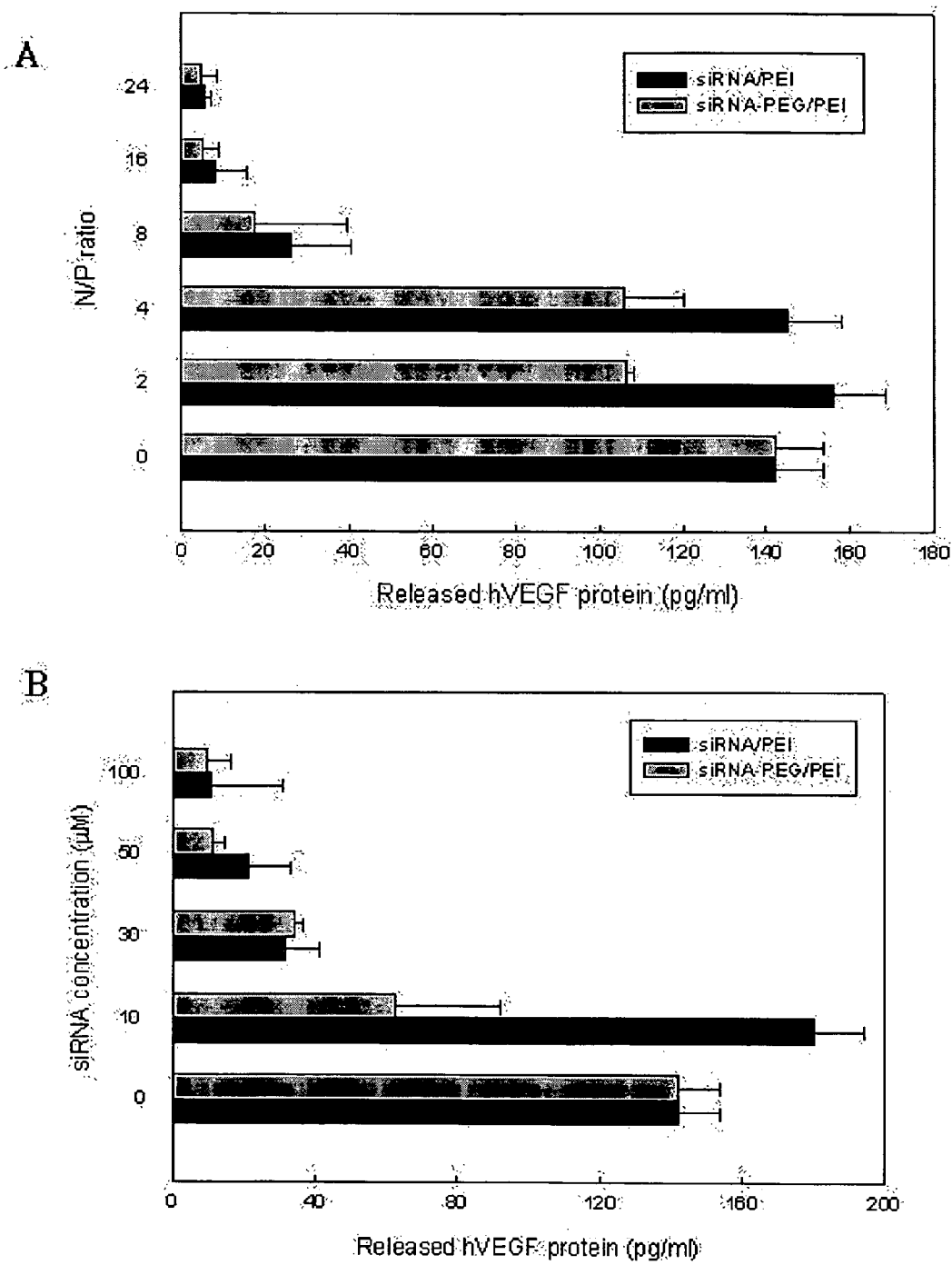
FIG. 11 is a graph showing suppression of VEGF gene expression as a function of N/P ratio, (A), and as a function of siRNA amount, (B), in the PC-3 cells treated with siRNA/PEI complexes (black bar) and siRNA-PEG/PEI polyelectrolyte complex micelles (gray bar).

According to another embodiment of the present invention, the siRNA-PEG/PEI polyelectrolyte complex micelles showed a strong resistance to nuclease-mediated siRNA degradation (see FIG. 10), and effectively suppressed the expression of VEGF of the human prostate cancer cell line (PC-3) in vitro (see FIG. 11). The VEGF gene suppression effect was even more evident when N/P ratio was increased or when the dose of siRNA was increased. Moreover, the siRNA-PEG polyelectrolyte complex micelles had the same effect on the inhibition of VEGF gene expression, regardless of the existence of serum (see FIG. 12), and the VEGF gene suppression induced by polyelectrolyte complex micelles exhibited a highly sequence-specific manner (see FIG. 13).

Influence of the siRNA on a tumor in an animal model was examined in another embodiment of the present invention. The results confirmed that tumor growth was inhibited to the various extent by the treatment of the VEGF siRNA, compared with a control group. Especially, the inhibitory activity of the VEGF siRNA-PEG/PEI polyelectrolyte complex micelles onto the tumor growth was more than that of the VEGF siRNA/PEI complex (see FIGS. 14 and 15).

The amount of VEGF protein and VEGF mRNA in the tumor confirmed that the VEGF siRNA-PEG/PEI polyelectrolyte complex micelles, unlike the VEGF siRNA/PEI complex, significantly suppressed the expression of VEGF protein (see FIG. 16), and the VEGF mRNA level in the tumor was completely suppressed by the treatment of VEGF siRNA-PEG/PEI polyelectrolyte complex micelles. A naked siRNA and an siRNA/PEI complex reduced the VEGF mRNA concentration slightly, while the scrambled siRNA polyelectrolyte complex micelle did not reduce the VEGF mRNA concentration at all (see FIG. 17). These results confirm that the polyelectrolyte complex micelles of the present invention are more advantageous to suppress VEGF expression in vivo than the siRNA/PEI complex.

The pronounced gene silencing effect of the siRNA-PEG/PEI polyelectrolyte complex micelles under the in vivo condition can be attributed to two unique structural characteristics of the polyelectrolyte complex micelles: (i) surface exposed PEG chains on the polyelectrolyte complex micelles to maintain their colloidal stability in the tissue fluid prior to cellular uptake, and (ii) specific intracellular cleavage of the siRNA-S—S-PEG conjugate in the cytosol after cellular uptake by endocytosis.

In another example of the present invention, the microvascular distribution in a tumor was examined by immunohistochemical staining. Compared with a control group, VEGF siRNA-PEG/PEI polyelectrolyte complex micelles had a substantially reduced number of microvessels in unit area of the tumor (see FIG. 18). This result indicates that vascular formation in the tumor is mainly dependent on the amount of VEGF in a solid tumor region. Therefore, the RNAi-mediated suppression of VEGF expression induced by VEGF siRNA-PEG/PEI polyelectrolyte complex micelles effectively reduces neovascular formation in the tumor, thereby significantly delaying the growth of the tumor.

Figure 19:
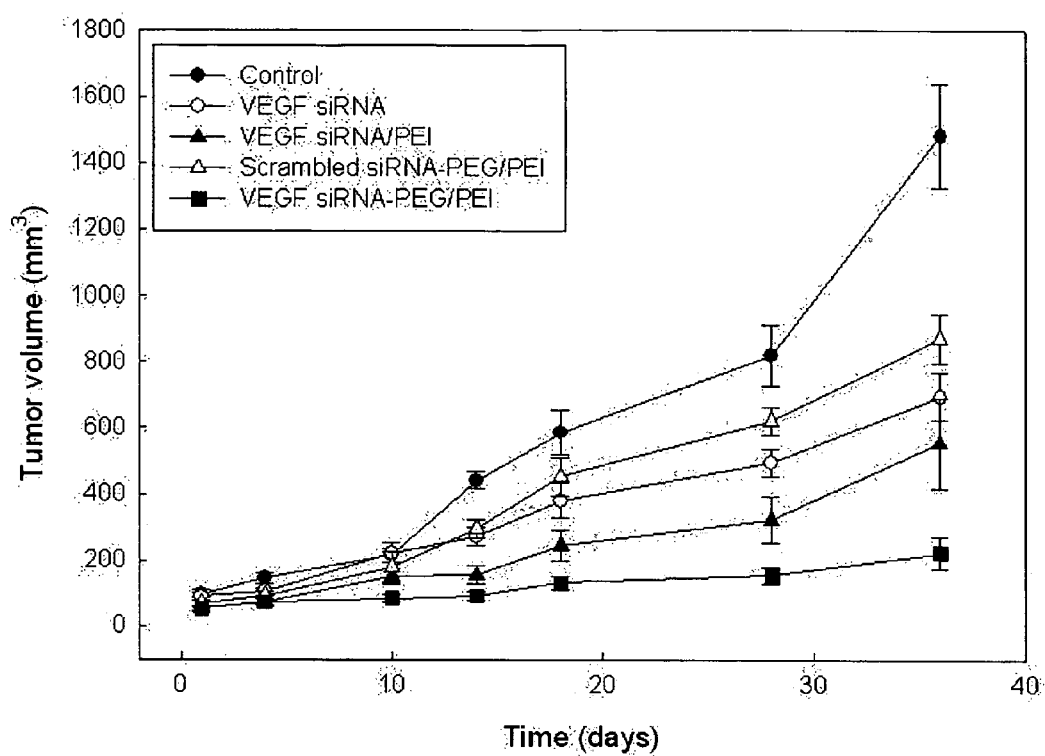
FIG. 19 is a graph showing the changes of tumor volume after systemic intravenous injection of various VEGF siRNA formulations.

In addition, according to still another example of the present invention, when VEGF siRNA-PEG/PEI polyelectrolyte complex micelles are administered systemically, they reduced the growth of the tumor cells more effectively than an siRNA formulation of the control group (see FIG. 19). Also, measurement of the amount of VEGF in the tumor reveals that the reduction in VEGF expression mainly occurred in the grafted PC-3 tumor treated with VEGF siRNA-PEG/PEI polyelectrolyte complex micelles (see FIGS. 20 and 21). These results show that VEGF siRNA-PEG/PEI polyelectrolyte complex micelles travels into the blood vessel for an extended time, and are accumulated more effectively in the tumor region by EPR (Enhanced Permeation and Retention) effect. It is well-known that nano-size carriers or polymer-conjugated drug is more easily accumulated in a tumor region through a loose vasculature. Thus, the passive tumor targeting of VEGF siRNA-PEG/PEI polyelectrolyte complex micelles is likely to influence the delay in tumor growth.

As described so far, hybrid conjugates are prepared by introducing a disulfide bond, various types of biodegradable linkage or non-cleavable linkage, for the conjugation between an anionic oligomer, siRNA molecule and a hydrophilic polymer. These hybrid conjugates are then interacted with other cationic polymers, lipids, peptides and the like to form polyelectrolyte complex micelles. According to the present invention, these polyelectrolyte complex micelles are useful as a cell delivery method for the siRNA molecules. Moreover, by introducing a cell specific ligand into the siRNA-PEG conjugate, alternative gene therapeutic effects can be improved. Especially when polyelectrolyte complex micelles using the siRNA-hydrophilic polymer conjugates containing a disulfide bond, and cationic polymers, lipids and peptides are employed, the cell delivery efficiency of the micelles was higher than that of siRNA alone. In addition, by using siRNA of VEGF as a target gene for the cancer therapy, it becomes possible to inhibit VEGF and suppress the proliferation of tumor in vivo. These results confirm that hVEGF siRNA-PEG/KALA polyelectrolyte complex micelles provide excellent suppression of cancer cell growth through suppression of VEGF expression, and exhibit a sharply improved stability in vivo.

EXAMPLES

The present invention will be described in more detail by referring to examples below, which are not intended to limit the present invention.

Example 1

Synthesis of siRNA-PEG Conjugate Containing Biodegradable Disulfide Bond

For Examples herein below, a hVEGF (human vascular endothelial growth factor) siRNA was used. A target sequence of the hVEGF siRNA is represented by SEQ ID NO: 1 (hVEGF, 189-207 bp), a sense strand of the hVEGF siRNA is represented by SEQ ID NO: 2, and an antisense strand of the hVEGF siRNA is represented by SEQ ID NO: 3. In addition, a sense strand of scrambled siRNA is represented by SEQ ID NO: 4, and an antisense strand of the scrambled siRNA is represented by SEQ ID NO: 5.

Figure 3:
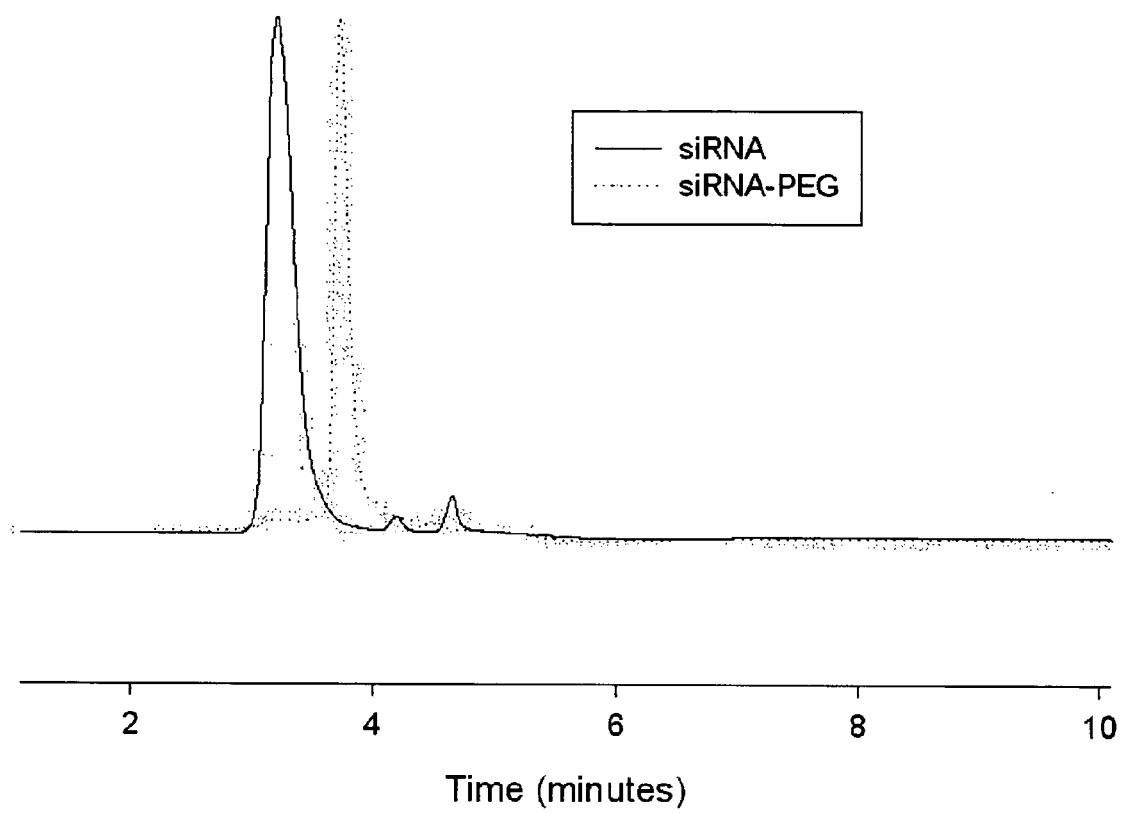
FIG. 3 is a chromatogram analyzing an siRNA-hydrophilic polymer conjugate containing a biodegradable disulfide bond and a naked siRNA with reversed phase HPLC.

Using an siRNA introduced an amine group at the 3' end of the sense strand of the siRNA (Qiangen Inc.) and SPDP which is a heterobifunctional and cleavable cross linker, a pyridyldithiol-activated siRNA intermediate (the amine at the end is activated to a pyridyldithiol group) was synthesized. First, 300 μg of the siRNA (20 mmol) dissolved in 800 μl of 5 mM phosphate buffer (pH=7.5) was mixed with 20 μl of 20 mM SPDP dissolved in dimethyl sulfoxide (DMSO) at room temperature for 30 minutes. The reactant thus obtained was dialyzed for 3 hours using dialysis membrane with a cut-off of 10,000 in 5 mM phosphate buffer (pH=7.5) to remove unreacted SPDP. Then, 100 μl of PEG-SH (molecular weight: 3,400, manufactured by Nektar, USA) dissolved in 5 mM phosphate buffer (pH=7.5) to a final concentration of 20 mM was added to the pyridyldithiol-activated siRNA intermediate, and was reacted at room temperature for 18 hours, thereby introducing a disulfide bond between the siRNA and the PEG. The mixture was then dialyzed again for 24 hours using dialysis membrane with a cut-off of 10,000 to remove unreacted PEG, and a desired siRNA-PEG conjugate containing a biodegradable disulfide bond was obtained. The siRNA-PEG conjugate thus synthesized was separated by a reversed phase HPLC(C-4). The siRNA-PEG conjugate was separated using a concentration gradient with 100 mM ammonium acetate and 50% acetonitrile (see FIG. 3).

Figure 4:
FIG. 4 is a photograph showing disulfide bond cleavage of an siRNA-hydrophilic polymer conjugate containing biodegradable disulfide bond in the presence of 10 mM glutathione similar to in vivo environment.

To evaluate the cleavability of the disulfide bond in the siRNA-S—S-PEG conjugate in a simulated intracellular condition, 0.5 μg of siRNA-PEG conjugate was incubated in 10 mM of glutathione media in a total volume of 25 μl. The cleavage reaction was allowed to proceed at 37° C. for 2 hours. The reaction was stopped by addition of 10 μl of gel loading buffer (0.25% (w/v) bromophenol blue and 40% (w/v) sucrose). The cleaved siRNAs were visualized by electrophoresis. As a result, siRNA was cleaved off from siRNA-PEG conjugate by GSH treatment, releasing intact forms of siRNA (FIG. 4). This indicates that intact siRNA can participate in RNAi reaction without any loss of activity.

Example 2

Figure 5:
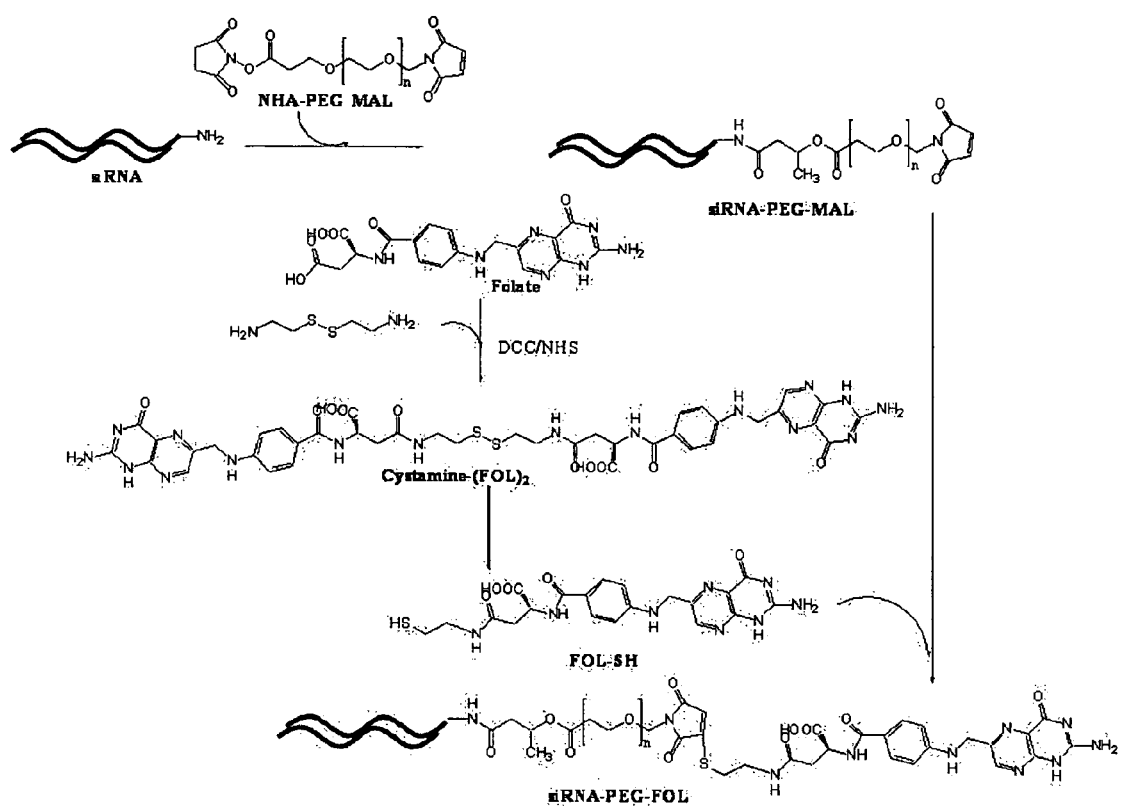
FIG. 5 is a schematic view describing the formation of a conjugate containing a non-cleavable linkage between an siRNA and a hydrophilic polymer such as PEG into which a cancer cell specific ligand (folate) is introduced.

Synthesis of siRNA-PEG Conjugate Containing Non-Cleavable Linkage into which Cancer Cell Selective Ligand is Introduced In order to introduce PEG having a cancer cell selective ligand into an siRNA through a non-cleavable linkage, an siRNA having an amine group (—NH$_2$) at the 3' end of the sense strand was used. First, 130 mg of folate (0.3 mmole) was dissolved in DMSO, and was mixed with 60 mg DCC (dicyclohexyl carbodiimide) and 34 mg of NHS (N-hydroxyl succinimide). The reaction was carried out at room temperature for 30 minutes, resulting in the activation of the carboxyl group of the folate. 34 mg of cystamine was added to the mixture and the reaction kept up for an additional 3 hours. At this time, the reaction molar stoichiometry between folate and cystamine was 2:1. The reactant thus obtained was dialyzed with water and any unreacted byproduct was removed. The reactant was then lyophilized. Next, cystamine-folate-cystamine (cystamine-FOL$_2$) was dissolved in aqueous DMSO solution (water:DMSO=50:50) to generate a free thiol group (—SH) in 0.1M 2-mercaptoethanol, obtaining folate-SH. 300 μg of the siRNA and 200 μg of the heterobifunctional PEG (e.g., NHS-PEG-MAL (maleimide)) were reacted for 1.5 hours in 10 mM sodium phosphate buffer to prepare siRNA-PEG-MAL having the PEG at the 3' end of the sense strand of the siRNA. Then, the siRNA-PEG-MAL and 0.1 mg of the folate-SH were mixed and reacted at room temperature for 3 hours. The reactant thus obtained was dialyzed with water using dialysis membrane with a cut-off of 5,000, and an siRNA-PEG-FOL conjugate was separated therefrom using a reversed phase HPLC(C-4) (FIG. 5).

Example 3

Formation of siRNA-PEG/KALA Polyelectrolyte Complex Micelle and its Characterization (1)

To obtain a gene transfer vehicle capable of transferring the siRNA-PEG conjugate synthesized and isolated in Example 1 to target cells, polyelectrolyte complex micelles were prepared using a cationic peptide such as KALA (Peptrone, Korea) or protamine (Sigma-Aldrich, USA), a cationic polymer such as PEI (Sigma-Aldrich, USA), or a cationic lipid such as dioleylphosphatidyl choline (DOPC, Nutfield, UK) and the like. Herein, formation of polyelectrolyte complex micelles using KALA is suggested as an example with detailed description, as follows. First, the siRNA-PEG conjugate (50 pmol) was diluted in an equal volume of 2×(PBS), and KALA dissolved in PBS was then added to the diluted conjugate to form polyelectrolyte complex micelles, followed by incubation at room temperature for 15 min to stabilize the formed micelles, wherein the ratio of positive charge of the KALA peptide to negative charge of the oligonucleotide was 1:1 (N/P=1/1).

The resulting siRNA-PEG/KALA polyelectrolyte complex micelles were analyzed for micellar size in an aqueous solution by DLS method. As a result, the siRNA-PEG/KALA polyelectrolyte complex micelles were found to have a very narrow size distribution with a size of about 150 nm (FIG. 6).

Example 4

Evaluation of Stability of siRNA-PEG/KALA Polyelectrolyte Complex Micelle Under Similar Conditions as In Vivo Three kinds of formulations consisting of a naked, non-modified siRNA, the siRNA-PEG conjugate synthesized in the Example 1, and the siRNA-PEG/KALA polyelectrolyte complex micelle prepared in the Example 3 were incubated for 0, 1, 2, 4, 8, 16, 24, and 48 hours, respectively, in culture mediums containing 10% FBS (fetal bovine serum) similar to the in vivo conditions, and stability of each formulation was evaluated to see how much the stability of the original siRNA molecule was improved. The resultant was evaluated by electrophoresis.

Figure 7:
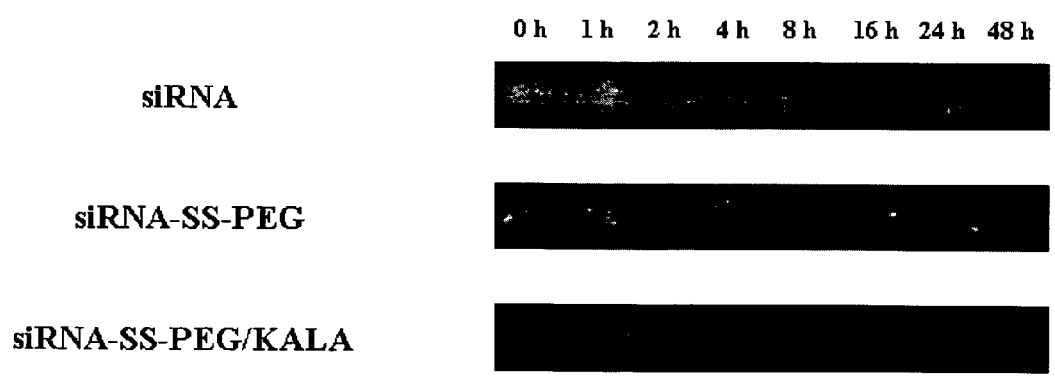
FIG. 7 is an electrophoresis photograph showing the degree of siRNA degradation in the presence of serum protein according to time, to evaluate the stabilities in blood using a naked siRNA, an siRNA-PEG conjugate, and an siRNA-PEG/KALA polyelectrolyte complex micelle, respectively.

It turned out that the stability of the siRNA-PEG conjugate was good after 24 hours, and was sharply increased for the siRNA-PEG/KALA polyelectrolyte complex micelle (FIG. 7).

Example 5

Effect of hVEGF siRNA-PEG/KALA Polyelectrolyte Complex Micelles on VEGF Expression in Prostate Cancer Cell Line In order to investigate the influence of hVEGF siRNA-PEG/KALA polyelectrolyte complex micelles on hVEGF expression in a prostate cancer cell line, the amount of hVEGF secreted by the human prostate cancer cells (PC-3) into culture medium was measured using enzyme-linked immunosorbent assay (ELISA). First, PC-3 cells were seeded to a 12-well plate at a density of $1 \times 10^5$ cells/well, and were cultured for 24 hours in the RPMI1640 medium containing 10% FBS. The culture medium was removed and changed again with a fresh RPMI1640 medium containing 10% FBS. Next, 10 pmol of hVEGF siRNA-PEG synthesized in the Example 1 was mixed with a cationic KALA peptide, wherein the ratio of negative charge to positive charge is 1:1 (N/P=1:1). The resulting mixture was incubated at room temperature for more than 15 minutes to form polyelectrolyte complex micelles. The PC-3 cells were then treated with optimum concentration of the polyelectrolyte complex micelles (10 pmol) in 1 ml of RPMI1640 medium at 37° C. for 4 hours. Later, the medium was changed with a fresh RPMI1640 medium containing 10% FBS, and the cells were incubated for an additional 6 hours. To quantify the amount of inhibited hVEGF, 1 ml of the RPMI1640 containing 10% FBS was added, and the total amount of secreted hVEGF for 18 hours at 37° C. was measured by ELISA. PC-3 cells treated with a hVEGF siRNA without PEG, an siRNA-PEG conjugate only, an siRNA/KALA complex, a polyelectrolyte complex micelle containing scrambled siRNA, and a polyelectrolyte complex micelle of green fluorescent protein (GEP) siRNA, respectively, and a PC-3 cell without any treatment were used as control groups.

Figure 8:
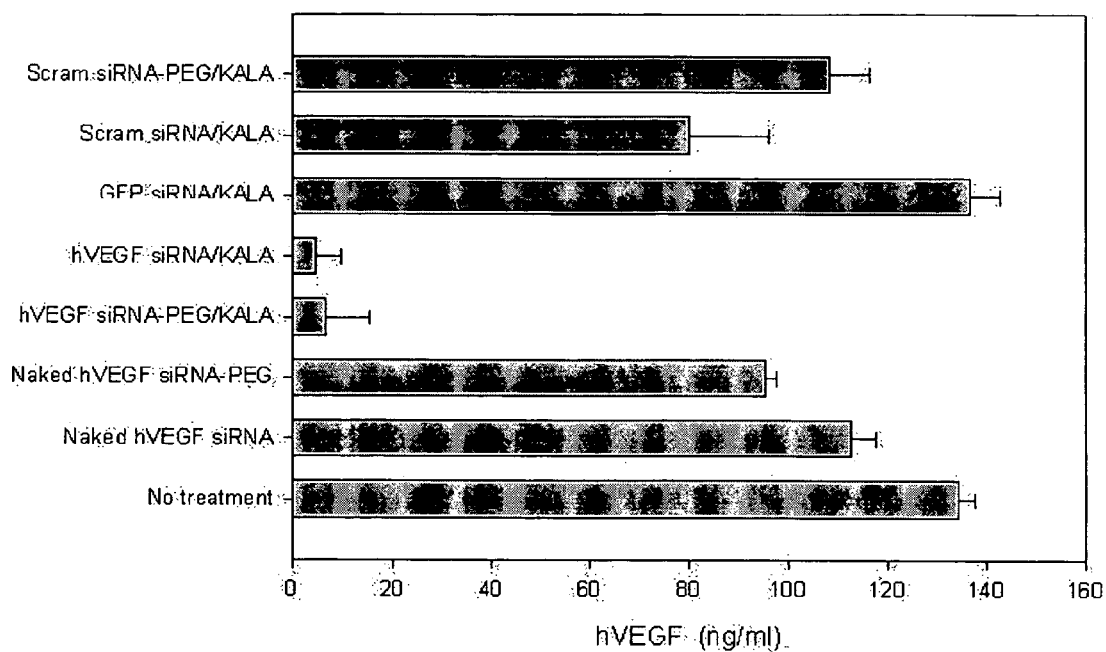
FIG. 8 is a graph showing the degree of suppression of VEGF expression in a human prostate cancer cell line (PC-3) by polyelectrolyte complex micelles produced from an interaction between hVEGF siRNA-PEG conjugate containing a biodegradable disulfide bond and KALA.

As a result, VEGF expression was substantially suppressed when the PC-3 cells were treated with the siRNA/KALA and the siRNA-PEG/KALA polyelectrolyte complex micelle (FIG. 8).

Example 6

Effect of hVEGF siRNA-PEG/KALA Polyelectrolyte Complex Micelles on Inhibition of Cancer Cell Growth in Animal Model To examine the inhibitory activity of hVEGF siRNA-PEG/KALA polyelectrolyte complex micelles on cancer cell proliferation in vivo, the siRNA formulations synthesized in the Example 1 and Example 3 were injected intravenously into the mice bearing human cancer cells, and the degree of cancer cell proliferation in each mouse was observed. To this end, $5 \times 10^6$ PC-3 cells were grafted through hypodermic administration to lumbar regions of 7-8 weeks old nude mice. When the tumor volume was reached to 0.1 cm$^3$, hVEGF siRNA-PEG/KALA, hVEGF siRNA/KALA, scrambled siRNA/KALA, and scrambled siRNA-PEG were injected intravenously into the mice, each at 7.5 µg at one time. Each of the formulations was administered at 1$^{st}$ and 10$^{th}$ days, and tumor sizes were measured on the 1$^{st}$, 3$^{rd}$, 5$^{th}$, 7$^{th}$, 10$^{th}$, 12$^{th}$, 14$^{th}$, and 18$^{th}$ days from the administration, respectively.

Figure 9:
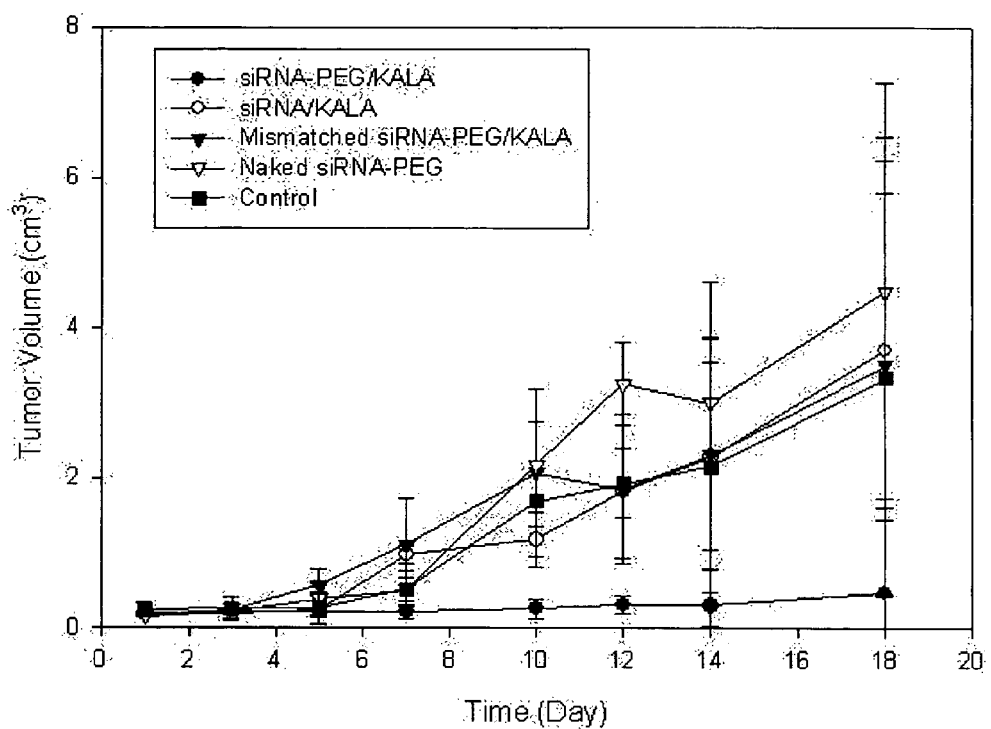
FIG. 9 is a graph showing the degree of tumor growth inhibition in an animal model into which a human prostate cancer cell line (PC-3) is grafted by polyelectrolyte complex micelles produced from an interaction between hVEGF siRNA-PEG conjugate containing a biodegradable disulfide bond and KALA.

As a result, the proliferation of cancer cells grafted into the animal was substantially suppressed when treated with the hVEGF siRNA-PEG/KALA polyelectrolyte complex micelles (FIG. 9).

Example 7

Formation of siRNA-PEG/KALA Polyelectrolyte Complex Micelle and its Characterization (2)

To prepare siRNA-PEG/PEI polyelectrolyte complex micelles, siRNA-PEG conjugate prepared in Example 1 was mixed with PEI (Sigma-Aldrich, USA) at an indicated N/P ratio and the mixture was left at room temperature for the formation of siRNA-PEG/PEI polyelectrolyte complex micelles.

Example 8

Serum Stability of siRNA-PEG Conjugates and Micelles Prepared Therefrom

Serum stabilities of naked siRNA, siRNA-PEG conjugate, and siRNA-PEG/PEI polyelectrolyte complex micelles were investigated by incubating each formulation (10 µg siRNA) in a medium containing 50% FBS (Gibco BRL, Grand Island, N.Y.). An aliquot was removed from the sample at an indicated time interval (0, 1, 2, 4, 8, 16, 24, and 48 h) and analyzed using a gel electrophoresis in tris-acetate buffer (1.2% agarose gel). siRNA-PEG/PEI polyelectrolyte complex micelles were pre-treated with heparin sodium salt solution (50 mg/ml) to obtain decomplexed siRNA-PEG conjugate by removing cationic PEI.

The unmodified siRNA showed almost complete degradation after 8 hours incubation in the serum containing medium (FIG. 10(a)). In contrast, the siRNA-PEG conjugate could last up to 16 hours without a significant loss of integrity in the same condition (FIG. 10(b)). For the siRNA-PEG/PEI polyelectrolyte complex micellar formulation, no detectable nuclease-mediated degradation of siRNA was monitored even after 48 hours incubation (FIG. 10(c)). This result suggests that the PEG conjugation alone could help to maintain the structural integrity of siRNA to some extent in the presence of serum. The prolonged protection observed in the polyelectrolyte complex micellar formulation was likely due to the presence of PEG chains in the outer shell layer that sterically hinder the access of nucleases into the siRNA/PEI internal core.

Example 9

Cell Culture and Transfection

Human prostate carcinoma cells (PC-3) were seeded to a 12-well plate at a density of $1.5 \times 10^5$ cells/well and allowed to attach for 24 hours. Prior to the transfection experiment, the growth medium were replaced with a pre-warmed serum free medium. Transfection was carried out by adding a desired siRNA formulation to the cells. After 4 hours, the transfection medium was replaced with a fresh serum-supplemented medium and incubated for 6 hours. The medium was then replaced with a fresh RMPI1640 medium containing 10% FBS and heparin (20 µg/ml). After 16 hours, the culture medium containing hVEGF was collected and centrifuged to remove cell debris. The amount of hVEGF secreted from the cells was determined by using Quantikine® hVEGF immunoassay kit (R&D Systems, Minneapolis, Minn.) following the manufacturer's instructions.

As a result, siRNA-PEG/PEI polyelectrolyte complex micelles efficiently reduced hVEGF expression in PC-3 cells. Compared to the siRNA/PEI complexes, the siRNA-PEG/PEI polyelectrolyte complex micelles demonstrated a higher inhibition level of hVEGF expression especially at lower N/P ratios (N/P ratios of 2 and 4, FIG. 11(A)). At the N/P ratio of 16, both formulations containing 50 pmol siRNA exhibited almost complete suppression of hVEGF secretion from PC-3 cells. The hVEGF expression was also inhibited in a dose-dependent manner (FIG. 11(B)).

Figure 12:
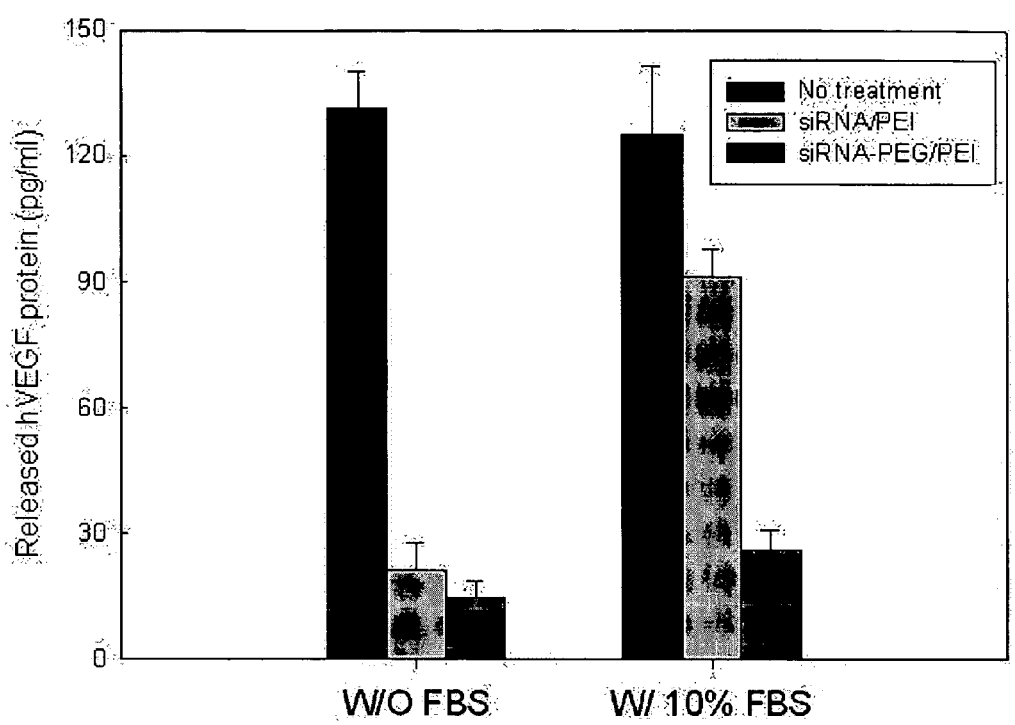
FIG. 12 is a graph showing the effect of 10% FBS on VEGF gene silencing in the PC-3 cells transfected with siRNA/PEI complexes (black bar) and siRNA-PEG/PEI polyelectrolyte complex micelles (gray bar). Control cells were not treated with siRNA (white bar).

Although there was no significant difference in the suppression of hVEGF expression between siRNA-PEG/PEI polyelectrolyte complex micelles and siRNA/PEI complexes in the absence of serum, they had quite different VEGF gene silencing effect in the presence of 10% FBS (FIG. 12). The siRNA-PEG/PEI polyelectrolyte complex micelles showed slightly reduced silencing extent of VEGF secretion with the addition of 10% FBS (from 14.6 to 25.9 pg/ml), whereas the siRNA/PEI complexes exhibited far smaller gene silencing effect under the same serum condition (from 21.2 to 91.3 pg/ml).

Example 10

Semi-Quantitative RT-PCR

To investigate whether the inhibition of hVEGF expression is resulted from decreased intracellular hVEGF mRNA, the cellular level of hVEGF mRNA was estimated by RT-PCR analysis. The PC-3 cells transfected with a desired formulation, including VEGF siRNA/PEI complexes, VEGF siRNA-PEG/PEI polyelectrolyte complex micelles (N/P=16), GFP siRNA/PEI complexes, scrambled siRNA/PEI complexes, scrambled siRNA-PEG/PEI polyelectrolyte complex micelles, were trypsinized and harvested after 16 hours incubation. Sense strand of GFP siRNA is represented by SEQ ID NO: 6, and antisense strand of GFP siRNA is represented by SEQ ID NO: 7. Total RNA was isolated by using RNeasy® Mini Kit (Qiagen, Valencia, Calif.) according to the manufacturer's instructions. Semi-quantitative RT-PCR was performed with the extracted total RNA (1 µg) using Super-Script™ III One-Step RT-PCR System with Platinum® Taq DNA Polymerase (Invitrogen, Carlsbad, Calif.). The thermal cycling condition for the RT-PCR was as follows: cDNA synthesis, 1 cycle at 55° C. for 25 min; denaturation, 1 cycle at 94° C. for 2 min; PCR amplification, 26 cycles at 94° C. for 20 s, at 60° C. for 30 s, and at 72° C. for 30 s; final extension, 1 cycle at 70° C. for 5 min. The PCR primers to detect hVEGF and human β-actin were obtained from Bioneer Co. (Daejeon, South Korea). Primers for detection of hVEGF are represented by SEQ ID NOS: 8 and 9, and primers for detection of human β-actin are represented by SEQ ID NOS: 10 and 11. The lengths of the PCR products for hVEGF and β-actin were 522 bp and 1126 bp, respectively. The PCR products were analyzed by 0.8% agarose gel electrophoresis and visualized by staining with ethidium bromide.

Figure 13:
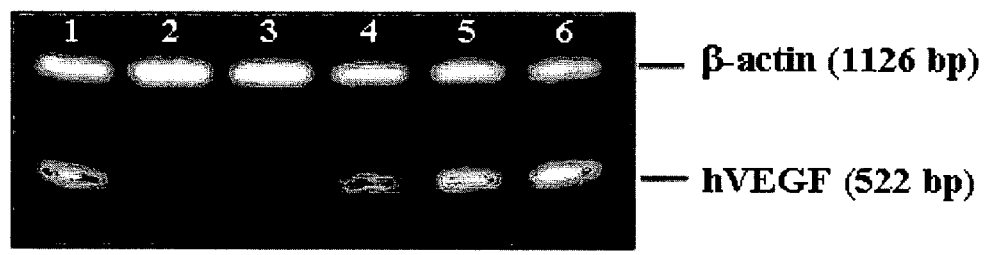
FIG. 13 is a photograph showing RT-PCR analysis showing down-regulation of VEGF mRNA in the PC-3 cells by VEGF siRNA-PEG/PEI polyelectrolyte complex micelles. Lane 1: no treatment; lane 2: VEGF siRNA/PEI complexes; lane 3: VEGF siRNA-PEG/PEI polyelectrolyte complex micelles; lane 4: GFP siRNA/PEI complexes; lane 5: scrambled siRNA/PEI complexes; and lane 6: scrambled siRNA-PEG/PEI polyelectrolyte complex micelles. Human-β-actin was used as a control. The transfection reaction was carried out in the medium containing 10% FBS.

As shown in FIG. 13, the VEGF siRNA-PEG/PEI polyelectrolyte complex micelles (lane 3) demonstrated a very faint VEGF mRNA band, but the samples containing siRNAs with a mismatched or irrelevant sequence to VEGF mRNA (scrambled siRNA and GFP siRNA) showed intact mRNA band intensities comparable to that of untransfected cells (lane 1). This result suggests that the VEGF siRNA-PEG/PEI polyelectrolyte complex micelles could silence VEGF expression at a post-transcriptional level in a highly sequence-specific manner.

Example 11

Verifying the Efficacy of siRNA in Mouse Model

Female nude mice (nu/nu) were obtained from Charles River (Wilmington, Mass.) and used when they were 7 weeks old. The animal tumor model was generated by the subcutaneous injection of human prostate carcinoma cells (PC-3, 1.5×106 cells) into a flank region of the mice. When the volume of the PC-3 tumor xenograft reached 50 mm3, the indicated siRNA formulations (i.e. hVEGF siRNA-PEG/PEI polyelectrolyte complex micelles (N/P ratio=16), hVEGF siRNA/PEI, naked hVEGF siRNA, and scrambled RNA-PEG/PEI) containing 500 pmoles of siRNA were intratumorally administered (day 1). Mock-treated control group was injected with PBS. An additional injection was performed at day 10. The size of tumors was monitored by measuring perpendicular diameters using a caliper. The tumor volume was determined based on the following formula as described in a previous publication (McPhillips, et. al., *Br. J. Cancer* 85:1753-1758 (2001)): tumor volume=(major axis)×(minor axis)2×(π/6). Statistical analysis was performed using a Student's t-test to evaluate the difference in tumor volumes. Statistical significance was defined as P<0.05.

Figure 14:
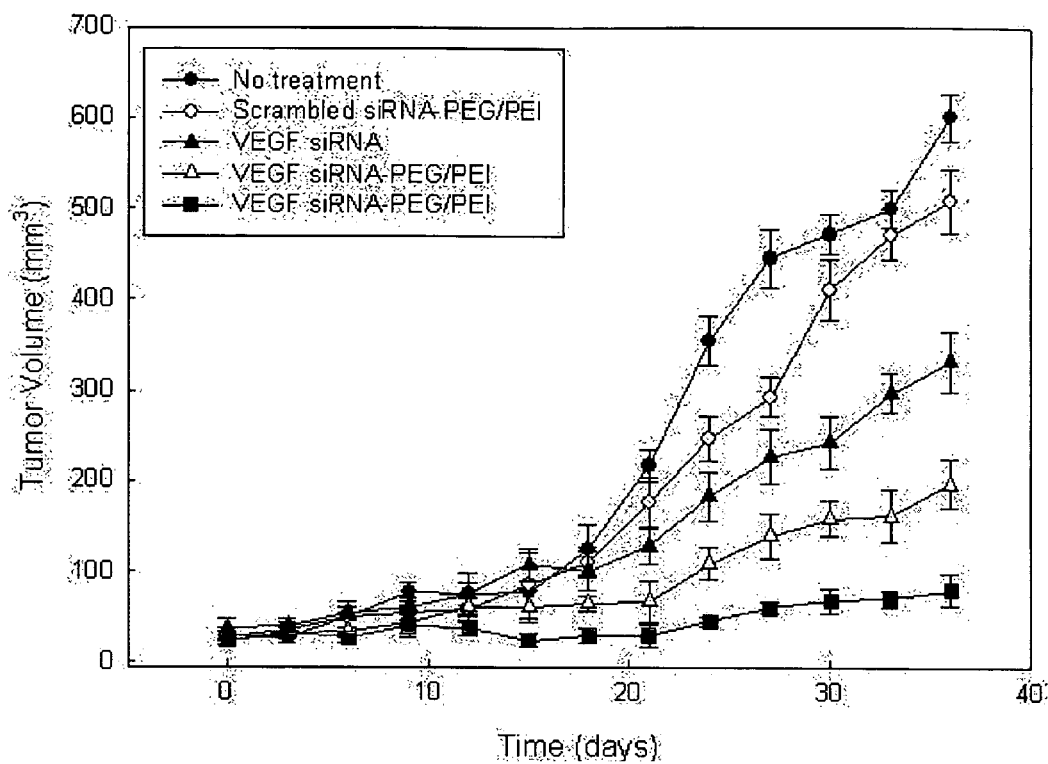
FIG. 14 is a graph showing VEGF gene silencing effect in the PC-3 cells transfected with various VEGF siRNA formulations.
Figure 15:
FIG. 15 is a photograph showing anti-tumor effect of various VEGF siRNA formulations after intratumoral injection into the PC-3 tumor xenografts treated with (a) PBS, (b) scrambled siRNA-PEG/PEI, (c) VEGF siRNA, (d) VEGF siRNA/PEI, and (e) VEGF siRNA-PEG/PEI.

As a result, all three hVEGF siRNAs treatments showed varying extents of tumor growth retardation, as compared with the control groups, scrambled RNA-PEG/PEI and PBS solution (FIGS. 14 and 15). Among the three siRNA formulations, the hVEGF siRNA-PEG/PEI polyelectrolyte complex micelles significantly retarded the tumor growth to a greater extent than the hVEGF siRNA/PEI complexes. Naked siRNA also showed some extent of RNAi-mediated gene silencing effect under the intratumoral condition due to its own sequence-specific gene silencing activity at the local injection site. At day 38 post-injection, the relative tumor volumes for siRNA-PEG/PEI polyelectrolyte complex micelles, siRNA/PEI complexes, naked siRNA were reduced to 13.3%, 32.8%, and 55.4%, respectively, as compared to the control injection of PBS solution (100%).

Example 12

Quantification of the Amount of Intratumoral hVEGF Protein and mRNA

To determine the amount of hVEGF in a solid tumor region, the solid tumor was harvested from the tumor-bearing mice 3 days after the day 10 treatment of the siRNA formulations. The tumors was weighed and homogenized in PBS by electronic tissue homogenizer (Kinematica AG, Switzerland). The tissue homogenates were centrifuged for 5 min at 3,000 rpm (4° C.) and the supernatant was stored for further analysis. The amount of hVEGF was determined by ELISA (Quantikine® human VEGF immunoassay kit, R&D Systems, Minneapolis, Minn.).

Figure 16:
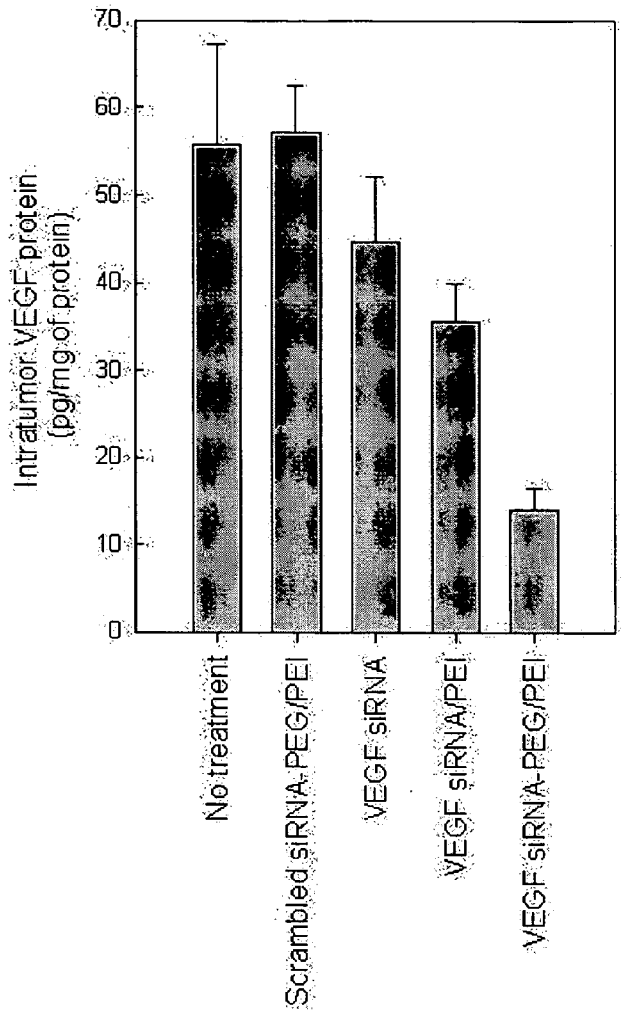
FIG. 16 is a graph showing intratumoral VEGF protein amount after treating with various siRNA formulations.
Figure 17:
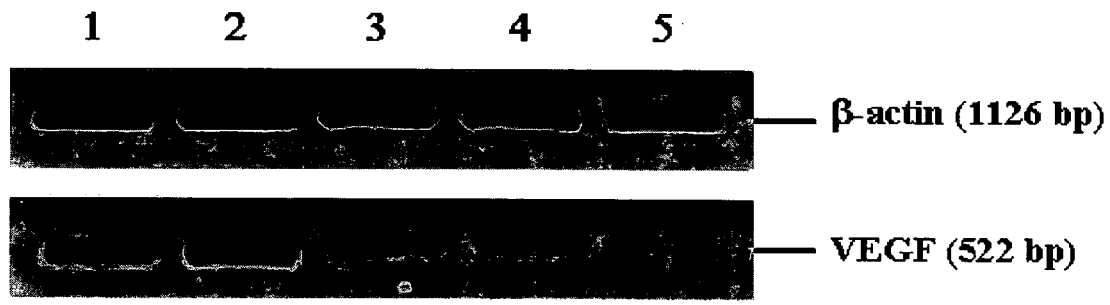
FIG. 17 is an electrophoresis photograph showing intratumoral VEGF mRNA level determined by RT-PCR analysis: Human β-actin was used as a control. Lane 1: no-treatment; lane 2: scrambled siRNA-PEG/PEI; lane 3: non-modified VEGF siRNA; lane 4: VEGF siRNA/PEI; and lane 5: VEGF siRNA-PEG/PEI.

As a result, the siRNA-PEG/PEI polyelectrolyte complex micelles (N/P ratio=16) suppress VEGF expression significantly more than VEGF siRNA/PEI complexes (FIG. 16). The polyelectrolyte complex micelles, the siRNA/PEI complexes, and naked siRNAs showed 74.8%, 36.3%, and 20.0% reduction in the amount of VEGF, respectively, compared to the PBS control (100%). In contrast, no significant inhibition of VEGF expression was detected for scrambled RNA-PEG/PEI polyelectrolyte complex micelles.

To determine intratumoral level of VEGF mRNA, total RNA was isolated from the tumor tissue by using RNeasy® Mini Kit (Qiagen, Valencia, Calif.), according to the manufacturer's recommendation. Semi-quantitative RT-PCR was performed using a SuperScript™ III One-Step RT-PCR kit (Invitrogen, Carlsbad, Calif.). The RT-PCR was carried out at the following thermal cycling conditions: cDNA synthesis, 1 cycle at 55° C. for 25 min; denaturation, 1 cycle at 94° C. for 2 min; PCR amplification, 26 cycles at 94° C. for 20 s, at 60° C. for 30 s, and at 72° C. for 30 s; final extension, 1 cycle at 70° C. for 5 min. The PCR primers to detect hVEGF and human β-actin were purchased from Bioneer, Inc. (Daejeon, Korea). The PCR products were separated in 0.8% agarose gel by electrophoresis and visualized by staining with ethidium bromide.

As a result, intratumoral hVEGF mRNA level was completely down-regulated with the hVEGF siRNA-PEG/PEI polyelectrolyte complex micelles. Naked siRNA and siRNA/PEI complexes slightly decreased VEGF mRNA levels, while sequence-mismatched siRNA polyelectrolyte complex micelles did not. These results clearly show the advantage of using the polyelectrolyte complex micelles for in vivo gene silencing of hVEGF expression over the siRNA/PEI complexes.

Example 13

Immunohistochemical Staining and Analysis of Microvessels in Solid Tumor Region

On day 28, the tumor-bearing mice were sacrificed for immunohistochemical staining. The solid tumor region was harvested, fixed in a 10% phosphate-buffered formaldehyde solution, and embedded in paraffin. The paraffin-embedded tumor tissues were sectioned in 3 micrometer-slices and stained using an antibody against Von Willebrand factor (Factor VIII). The sections were deparaffinized in xylene, rehydrated in graded ethanol (100%, 95%, 70%, and 50%) and finally submerged in PBS. Pretreatment for epitope retrieval and immunostaining was carried out on an automated immunostainer (Ventana ES, Ventana Medical Systems, Tucson, Ariz.). The pretreatment and staining conditions were as follows. The enzyme-induced epitope retrieval was then carried out by treating hydrated sections with protease 2 (20 μg/ml) for 4 min. The sections were incubated with a primary antibody that recognizes mouse Factor VIII (rabbit monoclonal IgG, Dako Cytomation, Carpinteria, Calif.) at 1:100 dilution for 30 min at room temperature and then incubated with a biotin-labeled anti-rabbit IgG (1:300 dilution, Sigma, St. Louis, Mo.) for 30 min at room temperature. The colorimetric detection of microvessels was performed by using the IView DAB detection kit (Ventana Medical Systems), following the manufacturer's recommendation. The tissue sections were counterstained with hematoxylin (Ventana Medical Systems) and dehydrated in graded ethanol (50%, 70%, 95%, and 100%).

To determine intratumoral microvessel density, the five independent areas (microscope field: 2.3 mm×3 mm, 6.9 mm$^2$) within the stained section were randomly selected and the images of the area were obtained at a magnification of 100× under a phase-contrast microscope equipped with CCD camera. The Factor VIII-positive microvessels were counted from the selected areas and a mean intratumoral microvessel density was calculated by the following formula: microvessel density (the number of Factor VIII-positive vessel/mm$^2$)=(the number of Factor VIII-positive vessel)×6.9. Microvessel formation at the PC-3 tumor xenografted region was visualized by staining with an antibody against Von Willebrand factor (Factor VIII).

Figure 18:
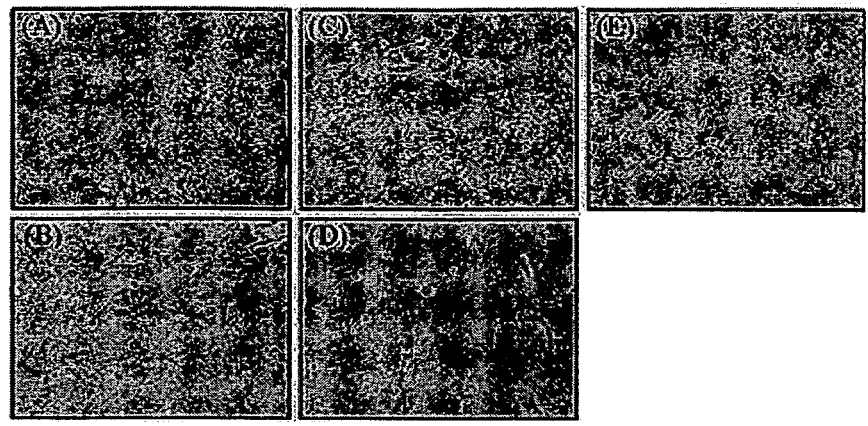
FIG. 18 is a photograph showing immunohistochemcal images of the PC-3 tumor xenografts: treated with (A) PBS, (B) scrambled siRNA-PEG/PEI, (C) non-modified VEGF siRNA, (D) VEGF siRNA/PEI, and (E) VEGF siRNA-PEG/PEI. A graph showing intratumoral microvessel density analysis of the PC-3 tumor is shown in (F).
Figure 18:
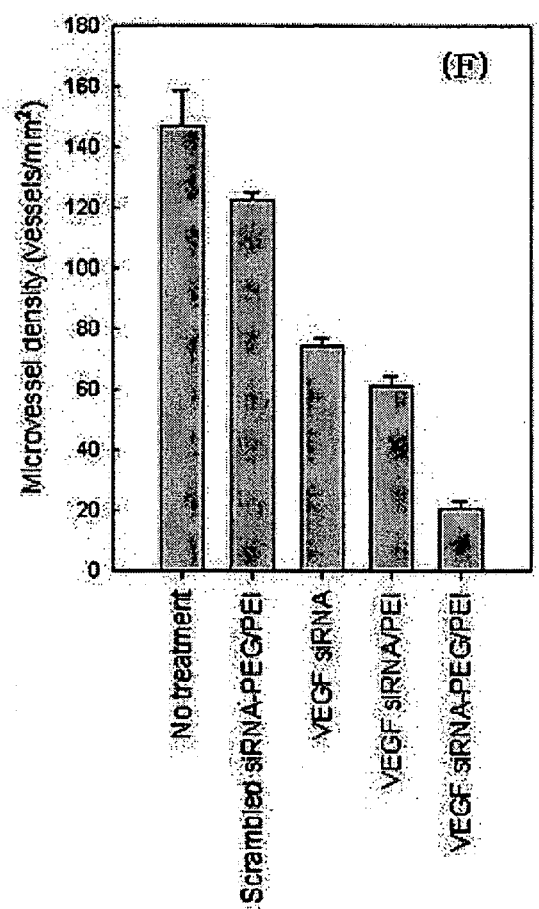

The group of tumors treated with VEGF siRNA-PEG/PEI polyelectrolyte complex micelles (N/P ratio=16) demonstrated remarkable reduction in the number of intratumoral micro-vessels per unit area, compared to control groups (FIG. 18). The results demonstrate the intratumoral angiogenic activity depends mainly on the amount of VEGF in the solid tumor region. Taken together, the RNAi-mediated suppression of VEGF expression by VEGF siRNA-PEG/PEI polyelectrolyte complex micelles effectively reduced the extent of intratumoral neovascularization, resulting in the significant retardation of tumor growth.

Example 14

Effect of hVEGF siRNA-PEG/PEI Polyelectrolyte Complex Micelles on Inhibition of Cancer Cell Growth in Animal Model by Systemic Administration To further validate the anti-tumor effect of siRNA-PEG/polyelectrolyte complex micelles for systemic administration, they were injected through tail vein of PC-3 tumor xenografted nude mice five times (day 1, 4, 10, 18, and 28). A twenty microgram dose of siRNA was intravenously injected as a single dose at each injection time.

Figure 20:
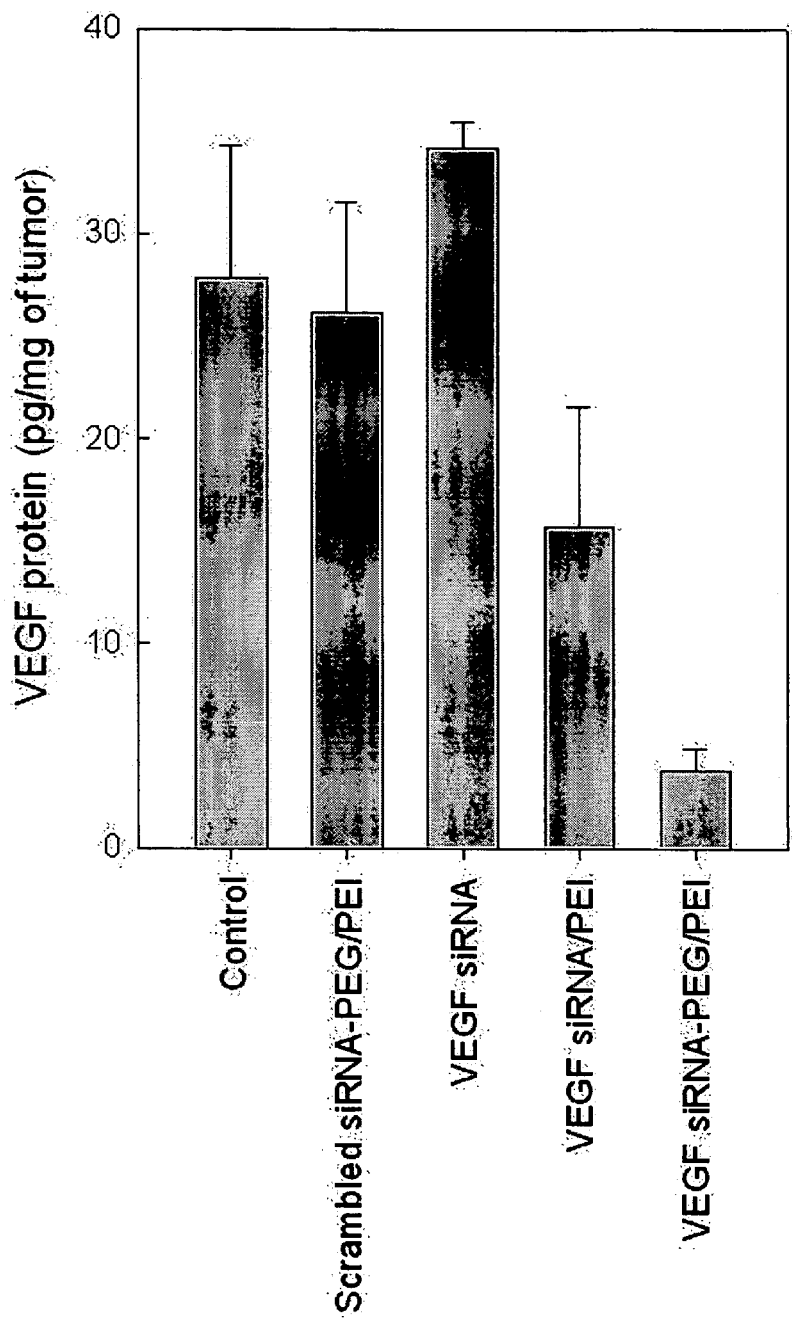
FIG. 20 is a graph showing the amount of VEGF protein after systemic intravenous injection of various VEGF siRNA formulations.
Figure 21:
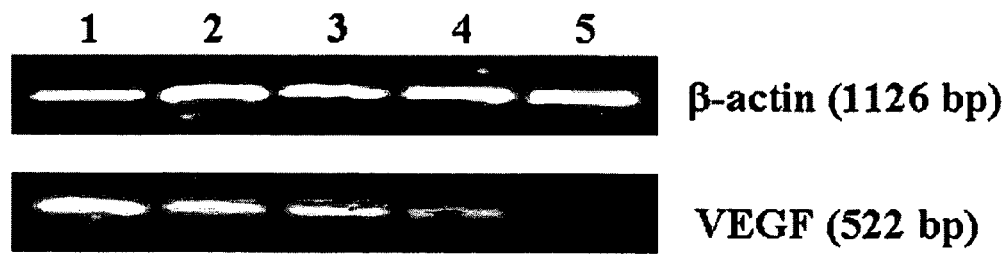
FIG. 21 is a graph showing the results obtained by RT-PCR upon VEGF mRNA amounts in a tumor after diverse VEGF siRNA formulations were administered to a whole body through intravenous administration, in which a human β-actin was used as a control group. Lane 1: PBS; lane 2: scrambled siRNA-PEG/PEI; lane 3: non-modified VEGF siRNA; lane 4: VEGF siRNA/PEI; and lane 5: VEGF siRNA-PEG/PEI.

The systemic injection of VEGF siRNA-PEG/PEI polyelectrolyte complex micelles reduced effectively the tumor growth, as compared with those of the control siRNA formulations (FIG. 19). The intratumoral amount of VEGF also showed that the reduced VEGF expression predominantly occurred in the PC-3 tumor xenograft treated with the polyelectrolyte complex micelle formulation (FIGS. 20 and 21). The results revealed that the VEGF siRNA-PEG/PEI polyelectrolyte complex micelles could circulate in the blood stream in a more prolonged manner and were efficiently accumulated in the tumor site by enhanced permeation and retention (EPR) effect.

INDUSTRIAL APPLICABILITY

In conclusion, the siRNA-hydrophilic polymer conjugates and polyelectrolyte complex micelles of the present invention can be advantageously used for improving stability of the siRNA molecules in vivo. Thus, it is now possible to deliver the siRNA molecules for therapeutic applications into cells more easily, and the siRNA molecules are very active even if small doses of the siRNA are used. Accordingly, the siRNA-hydrophilic polymer conjugates and polyelectrolyte complex micelles derived therefrom can be employed as a new siRNA delivery tool not only for therapeutic applications for cancer and other infectious diseases, but also for basic researches for bioengineering and medical industries.

It is to be appreciated that the Detailed Description section, and not the Summary and Abstract sections, is intended to be used to interpret the claims. These examples illustrate possible compositions used in the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A polyelectrolyte complex micelle comprising an siRNA-hydrophilic polymer conjugate and a cationic compound, wherein an end of the siRNA in the siRNA-hydrophilic polymer conjugate is covalently linked to a hydrophilic polymer via cleavable linkage, wherein a polyelectrolyte complex micelle is formed, and wherein the cationic compound is a cationic lipid.

2. The polyelectrolyte complex micelle according to claim 1, wherein the hydrophilic polymer is selected from the group consisting of polyethylene glycol, polyvinylpyrolidone, polyoxazolin and combinations thereof.

3. The conjugate according to claim 1, wherein the covalent bond (X) is a non-cleavable linkage.

4. The conjugate according to claim 3, wherein the non-cleavable linkage is an amide bond or phosphate bond.

5. The polyelectrolyte complex micelle according to claim 1, wherein the cleavable linkage is selected from the group consisting of a disulfide bond, acid-cleavable linkage, ester bond, anhydride bond, biodegradable bond and enzyme-cleavable linkage.

6. The polyelectrolyte complex micelle according to claim 1, wherein the 3' end of the siRNA molecule in the siRNA-hydrophilic polymer conjugate is covalently linked to the hydrophilic polymer.

7. The polyelectrolyte complex micelle according to claim 1, wherein the siRNA decreases expression of a gene selected from the group consisting of c-myc, c-myb, c-fos, c-jun, c-raf, and c-src.

8. A method of preparing the siRNA-hydrophilic polymer conjugate of claim 1, the method comprising: selecting a predetermined siRNA molecule having a functional group; and covalently bonding the siRNA molecule to a hydrophilic polymer.

9. The method according to claim 8, wherein the covalently bonding comprises: activating the functional group of siRNA; and covalently bonding the activated functional group to a hydrophilic polymer.

10. The method according to claim 9, wherein the functional group is selected from the group consisting of an amine group, thiol group, phosphate group and combinations thereof.

11. The method according to claim 9, wherein the functional group of siRNA is activated using a material selected from the group consisting of 1-ethyl-3,3-diethylaminopropyl carbodiimide, imidazole, N-hydrosuccinimide, dichlorohexylcarbodiimide, N-β-maleimidopropionic acid, N-β-maleimidopropyloxylsuccinimide ester, and N-succinimidylpyridyldithio propionate.

12. The polyelectrolyte complex micelle according to claim 1, wherein the siRNA decreases expression of a gene selected from the group consisting of bcl-2, vascular endothelial growth factor (VEGF), VEGF-B, VEGF-C, VEGF-D and PlGF.

* * * * *

```
                        SEQUENCE LISTING

<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: Synthetic target sequence of the hVEGF siRNA

<400> SEQUENCE: 1
ggagtaccct gatgagatc                                                   19

<210> SEQ ID NO 2
<211> LENGTH: 21
<212> TYPE: DNA
<213> ORGANISM: Artificial Sequence
<220> FEATURE:
<223> OTHER INFORMATION: Synthetic sense strand of hVEGF siRNA
<220> FEATURE:
<221> NAME/KEY: misc_feature
<223> OTHER INFORMATION: Residues 1-19 are RNA

<400> SEQUENCE: 2
ggaguacccu gaugagauct t                                                21

<210> SEQ ID NO 3
<211> LENGTH: 21
<212> TYPE: DNA
<213> ORGANISM: Artificial Sequence
<220> FEATURE:
<223> OTHER INFORMATION: Synthetic antisense strand of hVEGF siRNA
<220> FEATURE:
<221> NAME/KEY: misc_feature
<223> OTHER INFORMATION: Residues 1-19 are RNA

<400> SEQUENCE: 3
gaucucauca ggguacucct t                                                21

<210> SEQ ID NO 4
<211> LENGTH: 21
<212> TYPE: DNA
<213> ORGANISM: Artificial Sequence
<220> FEATURE:
<223> OTHER INFORMATION: Synthetic sense strand of scrambled siRNA
<220> FEATURE:
<221> NAME/KEY: misc_feature
<223> OTHER INFORMATION: Residues 1-19 are RNA

<400> SEQUENCE: 4
acgcguaacg cgggaauuut t                                                21

<210> SEQ ID NO 5
<211> LENGTH: 21
<212> TYPE: DNA
<213> ORGANISM: Artificial Sequence
<220> FEATURE:
<223> OTHER INFORMATION: Synthetic antisense strand of scrambled siRNA
<220> FEATURE:
<221> NAME/KEY: misc_feature
<223> OTHER INFORMATION: Residues 1-19 are RNA
```

```
<400> SEQUENCE: 5
aaauucccgc guuacgcgut t                                              21

<210> SEQ ID NO 6
<211> LENGTH: 19
<212> TYPE: RNA
<213> ORGANISM: Artificial Sequence
<220> FEATURE:
<223> OTHER INFORMATION: Synthetic sense strand of GFP siRNA

<400> SEQUENCE: 6
aacuucaggg ucagcuugc                                                 19

<210> SEQ ID NO 7
<211> LENGTH: 19
<212> TYPE: RNA
<213> ORGANISM: Artificial Sequence
<220> FEATURE:
<223> OTHER INFORMATION: Synthetic antisense strand of GFP siRNA

<400> SEQUENCE: 7
gcaagcugac ccugaaguu                                                 19

<210> SEQ ID NO 8
<211> LENGTH: 20
<212> TYPE: DNA
<213> ORGANISM: Artificial Sequence
<220> FEATURE:
<223> OTHER INFORMATION: Synthetic forward primer to detect hVEGF

<400> SEQUENCE: 8
aggagggcag aatcatcacg                                                20

<210> SEQ ID NO 9
<211> LENGTH: 21
<212> TYPE: DNA
<213> ORGANISM: Artificial Sequence
<220> FEATURE:
<223> OTHER INFORMATION: Synthetic reverse primer to detect hVEGF

<400> SEQUENCE: 9
caaggcccac agggattttc t                                              21

<210> SEQ ID NO 10
<211> LENGTH: 23
<212> TYPE: DNA
<213> ORGANISM: Artificial Sequence
<220> FEATURE:
<223> OTHER INFORMATION: Synthetic forward primer to detect human
      beta-actin

<400> SEQUENCE: 10
gtggggcgcc ccaggcacca ggg                                            23

<210> SEQ ID NO 11
<211> LENGTH: 24
<212> TYPE: DNA
<213> ORGANISM: Artificial Sequence
<220> FEATURE:
<223> OTHER INFORMATION: Synthetic reverse primer to detect human
      beta-actin

<400> SEQUENCE: 11
ctccttaatg tcacgcacga tttc                                           24
```